US008715927B2

(12) United States Patent
Lloyd et al.

(10) Patent No.: US 8,715,927 B2
(45) Date of Patent: May 6, 2014

(54) INHIBITION OF DNA POLYMERASES TO AUGMENT CHEMOTHERAPEUTIC AND ANTIMICROBIAL AGENTS

(75) Inventors: R. Stephen Lloyd, Portland, OR (US); Irina G. Minko, Portland, OR (US); Amanda K. McCullough, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 273 days.

(21) Appl. No.: 13/131,936

(22) PCT Filed: Apr. 22, 2009

(86) PCT No.: PCT/US2009/041354
§ 371 (c)(1),
(2), (4) Date: May 31, 2011

(87) PCT Pub. No.: WO2010/065159
PCT Pub. Date: Jun. 10, 2010

(65) Prior Publication Data

US 2011/0236507 A1 Sep. 29, 2011

Related U.S. Application Data

(60) Provisional application No. 61/119,187, filed on Dec. 2, 2008.

(51) Int. Cl.

| | |
|---|---|
| ***C12Q 1/68*** | (2006.01) |
| *C12Q 1/48* | (2006.01) |
| *C12N 9/10* | (2006.01) |
| *C07H 21/00* | (2006.01) |
| *C07H 21/04* | (2006.01) |

(52) U.S. Cl.
USPC ......... 435/6.1; 435/6.11; 435/6.13; 435/6.18; 435/15; 435/193; 536/22.1; 536/24.1; 536/24.2; 536/24.3; 536/24.33

(58) Field of Classification Search
None
See application file for complete search history.

(56) References Cited

U.S. PATENT DOCUMENTS

| | | | | |
|---|---|---|---|---|
| 4,725,677 | A * | 2/1988 | Koster et al. | 536/25.34 |
| 5,166,140 | A | 11/1992 | Scanlon et al. | |
| 5,635,349 | A * | 6/1997 | LaMarco et al. | 435/6.18 |
| 6,406,850 | B2 * | 6/2002 | Volkers et al. | 435/6.12 |
| 6,946,455 | B2 * | 9/2005 | Sugiyama et al. | 514/183 |
| 2003/0017573 | A1 | 1/2003 | Friedberg et al. | |
| 2006/0216735 | A1 * | 9/2006 | Bishop et al. | 435/6 |

FOREIGN PATENT DOCUMENTS

| | | |
|---|---|---|
| WO | WO 02/09720 | 2/2002 |
| WO | WO 2007/001684 | 1/2007 |

OTHER PUBLICATIONS

Beaulieu, "Finger loop inhibitors of the HCV NS5B polymerase: Discovery and prospects for new HCV therapy" 9(5) Current Opinion in Drug Discovery & Development 618-626 (2006).*

Lin et al., "A rapid plate assay for the screening of inhibitors against herpesvirus DNA polymerases and processivity factors" 88 Journal of Virological Methods 219-225 (2000).*

Butler et al., "A Method to Assay Inhibitors of DNA Polymerase IIIC Activity" 142 Methods in Molecular Medicine 25-36 (Aug. 2008).*

Hartley et al., "SJG-136 (NSC 694501), a Novel Rationally Designed DNA Minor Groove Interstrand Cross-Linking Agent with Potent and Broad Spectrum Antitumor Activity. Part 1: Cellular Pharmacology, In vitro and Intitial In vivo Antitumor Activity" 64 Cancer Research 6693-6699 (2004).*

Cooper et al., "Postoperative Concurrent Radiotherapy and Chemotherapy for High-Risk Squamous-Cell Carcinoma of the Head and Neck," *N. Engl. J. Med.*, vol. 350:1937-1944, 2004.

Kumari et al., "Replication Bypass of Interstrand Cross-Link Intermediates by *Escherichia coli* DNA Polymerase IV," *J. Biol. Chem.*, vol. 283(41):27433-27437, 2008.

Minko et al., "Role for DNA Polymerase κ in the Processing of $N^2$-$N^2$-Guanine Interstrand Cross-Links," *J. Biol. Chem.*, vol. 283(25):17075-17082, 2008.

Noble et al., "Outcome of Trabeculectomy with Intraoperative Mitomycin C for Uveitic Glaucoma," *Can. J. Ophthalmol.*, vol. 42:89-94, 2007.

Noll et al., "Formation and Repair of Interstrand Cross-Links in DNA," *Chem. Rev.*, vol. 106(2):277-301, 2006.

O-Wang et al., "DNA Polymerase κ, Implicated in Spontaneous and DNA Damage-induced Mutagenesis, is Overexpressed in Lung Cancer," *Cancer Res.*, vol. 61:5366-5369, 2001.

Shen et al., "Intravesical Treatments of Bladder Cancer: Review," *Pharm. Res.*, vol. 25(7):1500-1510, 2008.

Verburg et al., "Reduction of Joint Damage in Severe Rheumatoid Arthritis by High-Dose Chemotherapy and Autologous Stem Cell Transplantation," *Arthritis Rheum.*, vol. 52(2):421-424, 2005.

* cited by examiner

*Primary Examiner* — Jennifer Dunston
*Assistant Examiner* — Nancy J Leith
(74) *Attorney, Agent, or Firm* — Klarquist Sparkman, LLP

(57) ABSTRACT

Disclosed herein is the identification of human DNA polymerase κ (pol κ) as the polymerase that mediates repair of DNA containing interstrand cros slinks (ICLs). The mechanism of action of a number of chemotherapeutic and antimicrobial agents is the induction of ICLs. Thus, provided herein is a method of enhancing the efficacy of a chemotherapeutic or antimicrobial agent in a subject, including selecting a subject in need of treatment with an ICL -inducing agent and administering to the subject an ICL-inducing agent and a therapeutically effective amount of an inhibitor of pol κ. Also provided is a composition for treating a hyperproliferative disease, an autoimmune disease or an infectious disease, comprising an ICL-inducing agent and an amount of an inhibitor of pol κ sufficient to enhance the efficacy of the ICL-inducing agent. Further provided is a method of identifying a DNA polymerase inhibitor.

19 Claims, 10 Drawing Sheets

FIG. 1A

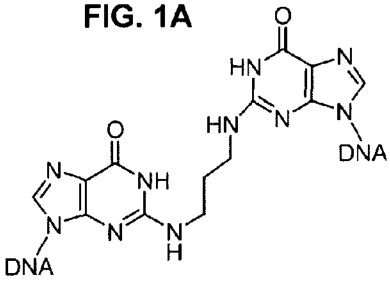

FIG. 1B

CpG ICL
5'-GCTAGCGAGTCC-3' (SEQ. ID. NO: 1)
3'-CCATGGTCGCTACGATCGCTCAGGTAGCGAACGTCC-5'(SEQ. ID. NO: 2)

GpC ICL
5'-GCTGAGCGATCC-3'(SEQ. ID. NO: 3)
3'-CCATGGTCGCTACGACTCGCTAGGTAGCGAACGTCC-5'(SEQ. ID. NO: 4)

FIG. 1C

ICL1
5' ⟶ 5'-GATGCTATCGTGTC(dd)-3'(SEQ. ID. NO: 5)
3'-GCTCAGCCATGGTCGCTACGATAGCACAGATAGCGA-5'(SEQ. ID. NO: 6)

ICL2
5' ⟶ 5'-CGTGTC(dd)-3' (nt 9-14 of SEQ. ID. NO: 5)
3'-GCTCAGCCATGGTCGCTACGATAGCACAGATAGCGA-5'(SEQ. ID. NO: 6)

ICL3
5' ⟶ 5'-GATGCTATCG-gl-3'(SEQ. ID. NO. 5) (nt 1-10 of SEQ. ID. NO: 5)
3'-GCTCAGCCATGGTCGCTACGATAGCACAGATAGCGA-5' (SEQ. ID. NO: 6)

ICL4
5' ⟶ 5'-CG-gl-3'
3'-GCTCAGCCATGGTCGCTACGATAGCACAGATAGCGA-5'(SEQ. ID. NO: 6)

ND1
5' ⟶
3'-GCTCAGCCATGGTCGCTACGATAGCACAGATAGCGA-5'(SEQ. ID. NO: 6)

ND2
5' ⟶ 5'-GATGCTATCGTGAG-3'(SEQ. ID. NO: 7)
3'-GCTCAGCCATGGTCGCTACGATAGCACAGATAGCGA-5'(SEQ. ID. NO: 6)

FIG. 1D

-10 primer: P32CGAGTCGGTACCAG-3'(SEQ. ID. NO: 8)
-1 primer: P32GGTACCAGCGATGCTAT-3'(SEQ. ID. NO: 9)
0(C) primer: P32GGTACCAGCGATGCTATC-3'(SEQ. ID. NO: 10)
0(A) primer: P32GGTACCAGCGATGCTATA-3'(SEQ. ID. NO: 11)
0(G) primer: P32GGTACCAGCGATGCTATG-3'(SEQ. ID. NO: 12)
0(T) primer: P32GGTACCAGCGATGCTATT-3'(SEQ. ID. NO: 13)
3'-GCTCAGCCATGGTCGCTACGATAGCACAGATAGCGA-5' (SEQ. ID. NO: 6)

FIG. 10

Template oligodeoxynucleotide:

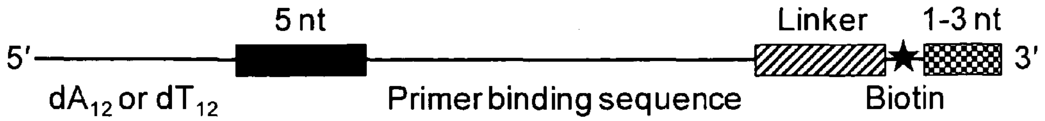

↓ Add primer to template oligodeoxynucleotide

↓ Raise temperature to ~70°C then cool to ~22°C

↓ Aliquot into 96-well dishes pre-coated with avidin

↓ Wash to remove excess template

↓ Add DNA polymerization buffer and DNA polymerase

↓ Add dNTPs and fluorescently labeled dNTP

↓ Add candidate inhibitor

↓ Raise temperature to 37°C for 30 minutes

↓ Wash all wells 3X with 20 mM EDTA to stop polymerization and remove unincorporated dNTPs ↓ Measure fluorescence

INHIBITION OF DNA POLYMERASES TO AUGMENT CHEMOTHERAPEUTIC AND ANTIMICROBIAL AGENTS

CROSS REFERENCE TO RELATED APPLICATIONS

This application is the U.S. National Stage of International Application No. PCT/US2009/041354, filed Apr. 22, 2009, published in English under PCT Article 21(2), which claims the benefit of U.S. Provisional Application No. 61/119,187, filed Dec. 2, 2008, which is herein incorporated by reference in its entirety.

STATEMENT OF GOVERNMENT SUPPORT

This invention was made with government support under contract number ES05355 awarded by the National Institutes of Health. The government has certain rights in the invention.

FIELD

This disclosure concerns the identification of human DNA polymerase κ (pol κ) as essential for repairing DNA containing interstrand crosslinks (ICLs) and the use of inhibitors of DNA polymerase, such as DNA polymerase κ, to enhance the efficacy of ICL-inducing agents for the treatment of hyperproliferative, autoimmune or infectious diseases.

BACKGROUND

The biological efficacy of interstrand crosslink (ICL)-inducing agents resides in their ability to prevent transient strand separation that is integral to DNA replication, RNA transcription, and recombination, making these bifunctional compounds effective antimicrobial and chemotherapeutic agents (Noll et al., *Chem. Rev.* 106:277-301, 2006; Lehoczky et al., *FEMS Microbiol. Rev.* 31:109-133, 2007). In addition, various endogenously generated bis-electrophiles, such as products of lipid peroxidation, are also capable of forming ICLs (Kozekov et al., *J. Am. Chem. Soc.* 125:50-61, 2003).

The processing and repair of ICLs in eukaryotic cells is extremely complex, potentially involving multiple DNA repair and damage tolerance pathways, including homologous recombination, nucleotide excision repair, translesion DNA synthesis, transcription-coupled repair, nonhomologous end joining, mismatch repair, cell cycle checkpoints, and ubiquitination/de-ubiquitination pathways (Noll et al., *Chem. Rev.* 106:277-301, 2006; Lehoczky et al., *FEMS Microbiol. Rev.* 31:109-133, 2007). The complexity of ICL repair and tolerance is further evident by data demonstrating that different organisms may preferentially use alternative pathways that are dependent on the stage of the cell cycle in which the ICL is encountered (Noll et al., *Chem. Rev.* 106: 277-301, 2006; Lehoczky et al., *FEMS Microbiol. Rev.* 31:109-133, 2007).

Although many models for ICL repair require the involvement of homologous recombination, an alternative, recombination-independent pathway exists that utilizes endonucleases for strand incision surrounding the ICL on one of the two DNA strands, and translesion synthesis (TLS) polymerases for gap-filling replication past the ICL site on the other strand (Wang et al., *Mol. Cell Biol.* 21:713-720, 2001; Zheng et al., *Mol. Cell Biol.* 23:754-761, 2003; Richards et al., *Nucleic Acids Res.* 33:5382-5393, 2005; Sarkar et al., *EMBO J.* 25, 1285-1294, 2006; Shen et al., *J. Biol. Chem.* 281:13869-13872, 2006; Liu et al., *Biochemistry* 45:12898-

12905, 2006). In these repair models, the dually-incised strand possesses sufficient mobility that a DNA polymerase can strand displace the nucleotide patch that is 5' to the lesion, then replicate past the ICL site to complete the repair gap-filling synthesis.

Insights into the essential genes for ICL repair and mutagenesis in *Saccharomyces cerevisiae* demonstrate a role for the product of rev3, the catalytic subunit of pol ζ (Henriques and Moustacchi, *Genetics* 95:273-288, 1980; Grossmann et al., *Mutat. Res.* 487:73-83, 2001). Further support for involvement of pol and another TLS polymerase, Rev1, in tolerance to ICL damage and their contribution to ICL-associated mutagenesis was obtained in both yeast (Sarkar et al., *EMBO J.* 25, 1285-1294, 2006; Wu et al., *Cancer Res.* 64:3940-3948, 2004) and vertebrate cells (Richards et al., *Nucleic Acids Res.* 33:5382-5393, 2005; Shen et al., *J. Biol. Chem.* 281:13869-13872, 2006; Nojima, et al., *Cancer Res.* 65:11704-11711, 2005).

Previous models for ICL repair have postulated the following sequential steps leading to restoration of an intact DNA strand: (i) DNA strand incision by components of nucleotide excision repair (NER); (ii) failure of pol ϵ to catalyze gap filling; (iii) monoubiquitination of proliferating cell nuclear antigen (PCNA); and (iv) recruitment of a TLS polymerase to replicate past the lesion and fill the gap (Sarkar et al., *EMBO J.* 25, 1285-1294, 2006). Despite previous investigations into the mechanisms of ICL repair, there remains a need to identify the specific enzymes involved in this type of repair process to improve treatments with ICL-inducing agents.

SUMMARY

It is disclosed herein that human DNA polymerase κ (pol κ) mediates repair of DNA containing interstrand crosslinks (ICLs). Since the mechanism of action of a number of chemotherapeutic and antimicrobial agents is the induction of ICLs, there is a need to inhibit the action of pol κ to minimize repair of ICLs in target cells (such as tumor cells). Thus, provided herein is a method of enhancing the efficacy of a chemotherapeutic or antimicrobial agent in a subject, including selecting a subject in need of treatment with an ICL-inducing agent and administering to the subject an ICL-inducing agent and a therapeutically effective amount of an inhibitor of pol κ sufficient to enhance efficacy of the ICL-inducing agent. Subjects in need of treatment with an ICL-inducing agent, include, for example, subjects diagnosed with a hyperproliferative disease, autoimmune disease or an infectious disease. Also provided is a method of treating a subject diagnosed with a hyperproliferative disease, autoimmune disease or an infectious disease, comprising administering to the subject a therapeutically effective amount of an ICL-inducing agent and an inhibitor of pol κ.

Further provided is a composition for treating a hyperproliferative disease, autoimmune disease or an infectious disease, comprising an ICL-inducing agent and an amount of an inhibitor of pol κ sufficient to enhance the efficacy of the ICL-inducing agent. Also provided is a method of identifying an agent that enhances the efficacy of an ICL-inducing agent, comprising screening candidate agents to identify an agent that inhibits activity of pol κ, thereby identifying an agent that enhances the efficacy of an ICL-inducing agent.

Also provided herein is a screening method to identify DNA polymerase inhibitors, such as inhibitors of DNA pol κ. The method includes mixing a template oligodeoxynucleotide, a primer oligodeoxynucleotide and the DNA polymerase; adding unlabeled dNTPs and a fluorescently-labeled dTTP or dATP; adding a candidate agent; and allowing the reaction to proceed for a sufficient period of time to allow DNA polymerization, wherein a reduction in incorporation of the fluorescently labeled dTTP or dATP in the presence of the inhibitor, relative to incorporation of the fluorescently labeled dTTP or dATP in the absence of the inhibitor, indicates the candidate agent is an agent the inhibits the activity of a DNA polymerase.

The foregoing and other features and advantages will become more apparent from the following detailed description of several embodiments, which proceeds with reference to the accompanying figures.

BRIEF DESCRIPTION OF THE FIGURES

FIG. 1A shows a structural model of an acrolein-derived $N^2$-$N^2$ guanine crosslink. FIG. 1B is a schematic of CpG and GpC crosslinked oligodeoxynucleotides used for mutagenesis assays. FIG. 1C is a schematic of the crosslinked (ICL) and non-damaged (ND) template oligodeoxynucleotides. Template deoxyguanosines associated with the crosslink and the corresponding unmodified deoxyguanosines are underlined. Arrows indicate the direction of DNA synthesis. To prevent DNA synthesis off of the shorter strand of the duplex oligodeoxynucleotide, either a 3'-glycerol unit (gl) or a dideoxycytidine (dd) was incorporated. To inhibit DNA synthesis off of the shorter strand in ND2, a double mismatch was placed at the end of the duplex region. FIG. 1D shows the sequences of primer oligodeoxynucleotides.

FIG. 10 is a schematic of an assay to identify inhibitors of DNA polymerases, such as pol κ. In this representative assay, the template oligodeoxynucleotide includes a poly dA or poly dT track followed by a 5 nucleotide (nt) segment of either T, C and G (if a poly dA track is used) or A, C and G (if a poly dT track is used). A biotinylated nucleotide (indicated by the star) is included 1 to 3 nucleotides prior to the 3' terminus.

SEQUENCE LISTING

Figure 2A:
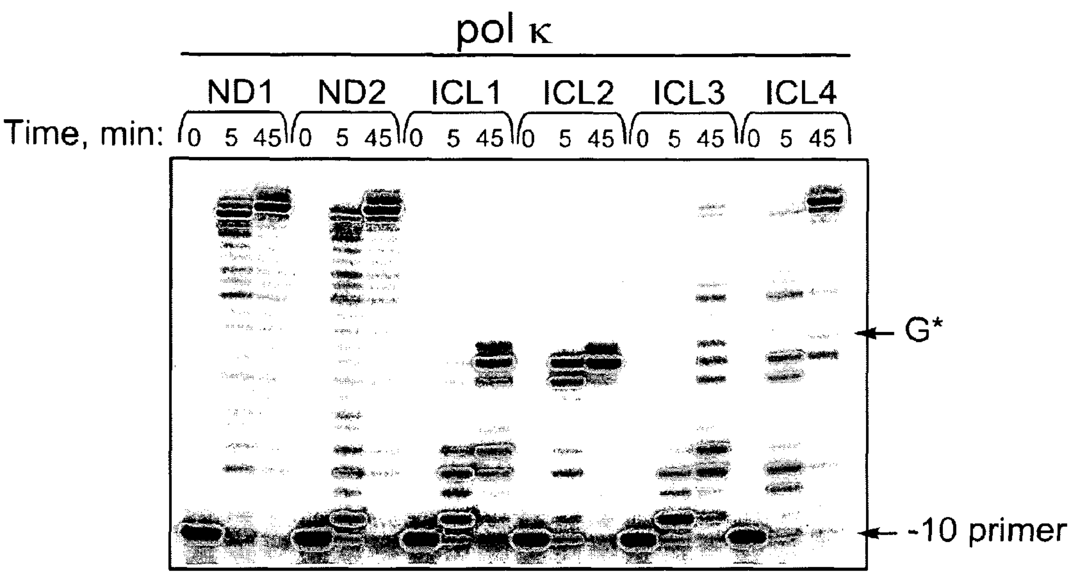
FIGS. 2A and 2B show primer extension assays of non-damaged (ND) and crosslinked (ICL) templates using human pol κ. Primer extensions by pol κ (2 nM) were conducted for a period of time as indicated (A). Single nucleotide incorporations by pol κ(1 nM) were carried out for 30 minutes (B).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 25, 2011, 4.34 KB, which is incorporated by reference herein. In the accompanying sequence listing:

SEQ ID NOS: 1-4 are the nucleotide sequences of the oligodeoxynucleotides used for mutagenesis assays.

SEQ ID NOS: 5-7 are the nucleotide sequences of the crosslinked and non-damaged template oligodeoxynucleotides.

SEQ ID NO: 8 is the nucleotide sequence of the −10 primer.

SEQ ID NO: 9 is the nucleotide sequence of the −1 primer.

SEQ ID NO: 10 is the nucleotide sequence of the 0(C) primer.

SEQ ID NO: 11 is the nucleotide sequence of the 0(A) primer.

SEQ ID NO: 12 is the nucleotide sequence of the 0(G) primer.

SEQ ID NO: 13 is the nucleotide sequence of the 0(T) primer.

SEQ ID NO: 14 is the nucleotide sequence of a primer for sequencing plasmid pMS2-ICL.

SEQ ID NO: 15 is the nucleotide sequence of a primer binding sequence used for identification of inhibitors of pol κ.

SEQ ID NO: 16 is the nucleotide sequence of a primer used for identification of inhibitors of pol κ.

SEQ ID NOs: 17-20 are the nucleotide sequences of pol κsiRNAs.

DETAILED DESCRIPTION

I. Abbreviations

ATP Adenosine triphosphate
cDNA Complementary DNA
CTP Cytidine triphosphate
DMSO Dimethylsulfoxide
DNA Deoxyribonucleic acid
dNTP Deoxyribonucleotide triphosphate
GTP Guanosine triphosphate HPLC High pressure liquid chromatography
ICL Interstrand cros slink
LB Luria-Bertani
MALDI Matrix-assisted laser desorption/ionization
MMC Mitomycin C
MS Mass spectrometry
ND Non-damaged
NER Nucleotide excision repair
NTP Nucleotide triphosphate
PAGE Polyacrylamide gel electrophoresis
PCNA Proliferating cell nuclear antigen
PCR Polymerase chain reaction
Pol Polymerase
RNA Ribonucleic acid
siRNA Small interfering RNA
TLS Translesion synthesis
TOF Time of flight II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 0-56081-569-8).

In order to facilitate review of the various embodiments of the disclosure, the following explanations of specific terms are provided:

Administration: The introduction of a composition into a subject by a chosen route. For example, if the chosen route is intravenous, the composition is administered by introducing the composition into a vein of the subject.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3rd Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

Antimicrobial agent: A compound that inhibits the growth, replication, spread or activity of a microorganism. In preferred embodiments, the antimicrobial agent is an ICL-inducing agent. In particular examples, the antimicrobial agent is a pyrrolobenzodiazepine, such as SJG-136, a heteroaromatic polycyclic antibiotic, such as GSQ1530, or mitomycin C.

Antisense inhibitor: Refers to an oligomeric compound that is at least partially complementary to the region of a target nucleic acid molecule to which it hybridizes. As used herein, an antisense inhibitor (also referred to as an "antisense compound") that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulation expression. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Autoimmune disease: A disease resulting from an aberrant immune response, such as the production of antibodies or cytotoxic T cells specific for a self antigen or a subject's own cells or tissues. Autoimmune diseases include, but are not limited to, diabetes mellitus type 1, systemic lupus erythematosis, Churg-Strauss Syndrome, multiple sclerosis, Graves' disease, idiopathic thrombocytopenic purpura and rheumatoid arthritis.

Avidin/Streptavidin: The extraordinary affinity of avidin for biotin allows biotin-containing molecules in a complex mixture to be discretely bound with avidin. Avidin is a glycoprotein found in the egg white and tissues of birds, reptiles and amphibia. It contains four identical subunits having a combined mass of 67,000-68,000 daltons. Each subunit consists of 128 amino acids and binds one molecule of biotin. Extensive chemical modification has little effect on the activity of avidin, making it especially useful for protein purification.

Another biotin-binding protein is streptavidin, which is isolated from *Streptomyces avidinii* and has a mass of 60,000 daltons. In contrast to avidin, streptavidin has no carbohydrate and has a mildly acidic pI of 5.5. Another version of avidin is NeutrAvidin Biotin Binding Protein (available from Pierce Biotechnology) with a mass of approximately 60,000 daltons.

The avidin-biotin complex is the strongest known non-covalent interaction ($Ka=10^{15}\ M^{-1}$) between a protein and ligand. The bond formation between biotin and avidin is very rapid, and once formed, is unaffected by extremes of pH, temperature, organic solvents and other denaturing agents.

Although examples disclosed herein use avidin as a specific binding agent, the avidin could be substituted with other types of avidin or streptavidin. The term "avidin" is meant to refer to avidin, streptavidin and other forms of avidin (such as derivatives or analogs thereof) that have similar biotin binding characteristics. Analogs or derivatives of avidin/streptavidin include, but are not limited to, nitro-streptavidin, non-glycosylated avidin, N-acyl avidins (such as N-acetyl, N-phthalyl and N-succinyl avidin), and the commercial products ExtrAvidin™ (Sigma-Aldrich), Neutralite Avidin (SouthernBiotech) and CaptAvidin (Invitrogen). Additional avidin/streptavidin analogs and derivatives are known in the art (see, for example, U.S. Pat. No. 5,973,124 and U.S. Patent Application Publication Nos. US 2004/0191832; US 2007/0105162; and US 2008/0255004).

Binding partner: Any molecule or composition capable of recognizing and specifically binding to a defined structural aspect of another molecule or composition. Examples of such binding partners and corresponding molecule or composition include biotin/avidin (such as biotin/streptavidin), antigen/antibody, hapten/antibody, and lectin/carbohydrate.

Biotin: A molecule (also known as vitamin H or vitamin $B_7$) that binds with high affinity to avidin and streptavidin. Biotin is often used to label nucleic acids and proteins for subsequent detection by avidin or streptavidin linked to a detectable label, such as a fluorescent or enzymatic reporter molecule. Biotinylation of a molecule (such as an antibody or other protein sample) is routinely achieved in the art by reacting a free carboxyl group on biotin with an amine group on a protein, such as an amine group found in an antibody or protein analyte/analog. Unless indicated otherwise, the term "biotin" includes derivatives or analogs that participate in a binding reaction with avidin. Biotin analogs and derivatives include, but are not limited to, N-hydroxysuccinimide-iminobiotin (NHS-iminobiotin), amino or sulfhydryl derivatives of 2-iminobiotin, amidobiotin, desthiobiotin, biotin sulfone, caproylamidobiotin and biocytin, biotinyl-ε-aminocaproic acid-N-hydroxysuccinimide ester, sulfo-succinimide-iminobiotin, biotinbromoacetylhydrazide, p-diazobenzoyl biocytin, 3-(N-maleimidopropionyl) biocytin, 6-(6-biotinamidohexanamido)hexanoate and 2-biotinamidoethanethiol. Biotin derivatives are also commercially available, such as DSB-X™ Biotin (Invitrogen). Additional biotin analogs and derivatives are known in the art (see, for example, U.S. Pat. No. 5,168,049; U.S. Patent Application Publication Nos. 2004/0024197, 2001/0016343, and 2005/0048012; and PCT Publication No. WO 1995/007466)

Biotin binding protein: A protein that binds biotin with sufficiently great affinity for an intended purpose. Examples of biotin binding proteins are well known in the art, and include avidin, streptavidin, NeutrAvidin, and monoclonal antibodies or receptor molecules that specifically bind biotin. In the context of this disclosure, avidin could be replaced with any other biotin-binding proteins, or a combination of biotin binding proteins.

Chemotherapeutic agent: An agent with therapeutic usefulness in the treatment of diseases characterized by abnormal cell growth or hyperplasia. Such diseases include cancer, autoimmune disease as well as diseases characterized by hyperplastic growth such as psoriasis. One of skill in the art can readily identify a chemotherapeutic agent (for instance, see Slapak and Kufe, *Principles of Cancer Therapy*, Chapter 86 in *Harrison's Principles of Internal Medicine,* 14th edition; Perry et al., *Chemotherapy*, Ch. 17 in Abeloff, *Clinical Oncology* $2^{nd}$ ed., ©2000 Churchill Livingstone, Inc; Baltzer L, Berkery R (eds): *Oncology Pocket Guide to Chemotherapy,* 2nd ed. St. Louis, Mosby-Year Book, 1995; Fischer DS, Knobf MF, Durivage HJ (eds): The Cancer Chemotherapy Handbook, 4th ed. St. Louis, Mosby-Year Book, 1993). Examples of chemotherapeutic agents include ICL-inducing agents, such as melphalan (ALKERAN™), cyclophosphamide (CYTOXAN™), cisplatin (PLATINOL™) and busulfan (BUSILVEX™, MYLERAN™).

Disease: An abnormal condition of an organism that impairs bodily functions.

DNA polymerase kappa (pol κ): A member of the Y-family of DNA polymerases, which can transverse replication-blocking DNA lesions, such as those created by reaction with epoxide intermediates of polycyclic aromatic hydrocarbons. Members of the Y-family of DNA polymerases do not have 3' to 5' exonuclease activity. Expression of Y-family polymerases is often induced by DNA damage. Pol κ and other Y-family polymerases are phylogenetically unrelated to classical DNA polymerases. Y-family polymerases are characterized by low fidelity replication using undamaged template and the ability to carry out translesion DNA synthesis. Pol κ, an ortholog of DinB, is able to bypass abasic and bulky DNA adduct lesions and make both base-substitution and frameshift mutations. The prokaryotic homolog of pol κ is DNA polymerase IV.

DNA repair: A collection of processes by which a cell identifies and corrects damage to the DNA molecules that encode its genome. In human cells, both normal metabolic activities and environmental factors such as UV light can cause DNA damage, resulting in as many as 1 million individual molecular lesions per cell per day. Many of these lesions cause structural damage to the DNA molecule and can alter or eliminate the cell's ability to transcribe the gene that the affected DNA encodes. Other lesions induce potentially harmful mutations in the cell's genome. Consequently, the DNA repair process must be constantly active so it can respond rapidly to any damage in the DNA structure.

The rate of DNA repair is dependent on many factors, including the cell type, the age of the cell, and the extracellular environment. A cell that has accumulated a large amount of DNA damage, or one that no longer effectively repairs damage incurred to its DNA, can enter one of three possible states: an irreversible state of dormancy, known as senescence; apoptosis or programmed cell death or unregulated cell division, which can lead to the formation of a tumor that is cancerous.

Efficacy: Refers to the ability of agent to elicit a desired therapeutic effect. Efficacy also refers to the strength or effectiveness of a compound. As used herein, "enhancing efficacy" means to increase the therapeutic action of an agent. For example, when the agent is a chemotherapeutic agent, "enhancing efficacy" generally refers to increasing the ability of the agent to kill target cells, such as tumor cells.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology,* $4^{th}$ ed., John Wiley & Sons, Inc., 1999.

Hyperproliferative disease: A disease or disorder characterized by the uncontrolled proliferation of cells. Hyperproliferative diseases include, but are not limited to malignant and non-malignant tumors and psoriasis.

Infectious disease: A disease caused by a pathogen, such as a fungus, parasite, bacterium or virus.

Isolated: An "isolated" biological component, such as a nucleic acid, protein or organelle that has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Interstrand crosslink (ICL): A covalent bond between two strands of a DNA molecule.

ICL-inducing agent: A compound that promotes the formation of ICLs in DNA. Examples of ICL-inducing agents include, but are not limited to, nitrogen mustards, mitomycin C, platinum compounds and psoralens. Nitrogen mustards are bifunctional alkylating agents and include, for example, chlorambucil, mechlorethamine, L-phenylalanine mustard and phosphamide mustard. Platinum compounds include, but are not limited to, cisplatin (PLATINOL™), also known as cis-Diamminedichlorophatinum (cis-DPP). Psoralens include, for example, trimethylpsoralen (TMP) and 8-methoxy-psoralen. Other ICL-inducing agents include diepoxybutane, melphalan (ALKERAN™), cyclophosamide (CYTOXAN™), SJG-136 (Pyrrolobenzodiazepine) and busulfan (BUSILVEX™, MYLERAN™).

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, cofactors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540 λ. Red fluorophores, for example Texas Red, Cy5 and tetramethylrhodamine, are characterized by their emission at wavelengths generally in the range of 590-690 λ.

Examples of fluorophores that may be used are provided in U.S. Pat. No. 5,866,366 to Nazarenko et al., and include for instance: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DAB CYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6- dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Linker: One or more nucleotides or amino acids that serve as a spacer between two molecules, such as between two nucleic acid molecules or two peptides.

Neoplasia, malignancy, cancer and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Oligodeoxynucleotide: A nucleic acid molecule comprising deoxyribonucleotides (nucleotides with a deoxy sugar) and generally having a length of 300 bases or fewer.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Primer: In the context of DNA synthesis, a "primer" is an oligonucleotide to which additional nucleotides can be added by a DNA polymerase.

Purified: The term purified does not require absolute purity; rather, it is intended as a relative term. Thus, for example, a purified peptide preparation is one in which the peptide or protein is more enriched than the peptide or protein is in its natural environment within a cell. In some embodiments, a preparation is purified such that the protein or peptide represents at least 50%, at least about 75%, at least about 90%, at least about 95% or at least about 99% of the total peptide or protein content of the preparation.

Screening: As used herein, "screening" refers to the process used to evaluate and identify candidate agents that exhibit a desired function or activity, such as agents that inhibit activity of pol κ.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Template: As used herein, a template strand or template oligodeoxynucleotide is a single-stranded oligonucleotide that determines the base sequence of a complementary strand during polymerization of a DNA duplex.

Therapeutically effective amount: A quantity of a specific substance sufficient to achieve a desired effect in a subject being treated. For instance, in some embodiments, a therapeutically effective amount of a pol κ inhibitor is the amount necessary to enhance the efficacy of an ICL-inducing agent.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

It is disclosed herein that human DNA polymerase κ (pol κ) contributes to the repair of DNA containing interstrand crosslinks (ICLs). Since the mechanism of action of a number of chemotherapeutic and some antimicrobial agents is the induction of ICLs, it has now been determined that inhibition of the action of pol κ reduces repair of ICLs in target cells (such as tumor cells). Thus, provided herein is a method for enhancing the efficacy of an interstrand crosslink (ICL)-inducing agent in a subject, comprising (i) selecting a subject in need of treatment with an ICL-inducing agent and (ii) administering to the subject an ICL-inducing agent and a therapeutically effective amount of an inhibitor of DNA polymerase kappa (pol κ) sufficient to enhance efficacy of the ICL-inducing agent. In some embodiments, the subject has a hyperproliferative disease (such as a tumor), an autoimmune disease or an infectious disease.

Further provided is a method of treating a subject diagnosed with a hyperproliferative disease, an autoimmune disease or an infectious disease, comprising administering to the subject a therapeutically effective amount of an interstrand crosslink (ICL)-inducing agent and an inhibitor of pol κ. In some embodiments, the ICL-inducing agent is a chemotherapeutic agent. The chemotherapeutic agent can be any type of chemotherapeutic agent that induces ICLs, such as, but not limited to trimethylpsoralen, nitrogen mustard, chlorambucil, mechlorethamine, phosphamide mustard, cisplatin (PLATI- NOL™), mitomycin C, diepoxybutane, melphalan (ALKERAN™), L-phenylalanine mustard, cyclophosamide (CYTOXAN™), 8-methoxy-psoralen, SJG-136 (pyrrolobenzodiazepine) and busulfan (BUSILVEX™, MYLERAN™). In particular examples, the chemotherapeutic agent is selected from melphalan, cyclophosphamide, cisplatin and busulfan.

In some embodiments of the methods, the ICL-inducing agent is an antimicrobial agent, such as a pyrrolobenzodiazepine (for example, SJG-136), a heteroaromatic polycyclic antibiotic (for example, GSQ1530) or mitomycin C. In particular embodiments, the ICL-inducing antimicrobial and pol κ inhibitor are applied topically to an infected area, such as a lesion in the skin, or the eye (for example, the conjunctiva) or via an abscess cavity.

In other embodiments, the ICL-inducing agent is applied topically or locally to an affected target area in the presence of a pol κinhibitor. For example, the pol κinhibitor can be applied with an ICL-inducing agent such as mitomycin C to an intra-operative bleb formed during glaucoma surgery to maintain patency of the bleb. Alternatively, the ICL-inducing agent (such as mitomycin C) is infused into the bladder to treat bladder tumors.

When the subject to be treated has an infectious disease, the infectious disease can be, for example, a bacterial infection or a viral infection. Hyperproliferative diseases include, for example, tumors, including malignant/cancerous tumors, and autoimmune diseases. In some embodiments, the autoimmune disease is rheumatoid arthritis, lupus, diabetes or multiple sclerosis. In some embodiments, the cancer (or malignant tumor) is a solid tumor or hematogenous cancer. In particular examples, the solid tumor is head and neck cancer, testicular cancer or ovarian cancer. In some examples, the hematogenous cancer is a myeloma or a leukemia.

The pol κinhibitor for use with the disclosed methods can be any type of molecule that inhibits expression or activity of pol κ. In some embodiments, the pol κinhibitor is a small molecule inhibitor, an antisense inhibitor or an antibody. In particular examples, the pol κ inhibitor is a small molecule inhibitor.

In some embodiments of the methods, the pol κinhibitor is administered to a subject in a single dose. In other embodiments, the pol κ inhibitor is administered in multiple doses. The dosing regimen of the pol κinhibitor will vary depending on a variety of factors, including the type of inhibitor being used and the disease to be treated. It is within the ability of one of skill in the art to determine an appropriate dose and dosing schedule for a pol κ inhibitor.

In some embodiments, the pol κ inhibitor is administered with the ICL-inducing agent. In other embodiments, the pol κ inhibitor is administered following the ICL-inducing agent. In some embodiments, the pol κ inhibitor is administered with the ICL-inducing agent and a subsequent dose (or doses) is administered to the patient following the initial dose.

Also provided herein is a composition for treating a hyperproliferative disease, an autoimmune disease or an infectious disease, comprising an ICL-inducing agent and an amount of an inhibitor of pol κ sufficient to enhance the efficacy of the ICL-inducing agent. In some embodiments, the composition further comprises a pharmaceutically acceptable carrier.

In some cases, the ICL-inducing agent of the composition is a chemotherapeutic agent. The chemotherapeutic agent can be any type of chemotherapeutic agent that induces ICLs, such as, but not limited to trimethylpsoralen, nitrogen mustard, chlorambucil, mechlorethamine, phosphamide mustard, cisplatin (PLATINOL™), mitomycin C, diepoxybutane, melphalan (ALKERAN™), L-phenylalanine mustard, cyclophosamide (CYTOXAN™), 8-methoxy-psoralen, SJG-136 (Pyrrolobenzodiazepine) and busulfan (BUSILVEX™, MYLERAN™). In particular examples, the chemotherapeutic agent is selected from melphalan, cyclophosphamide, cisplatin and busulfan.

In some embodiments of the methods, the ICL-inducing agent is an antimicrobial agent, such as a pyrrolobenzodiazepine (for example, SJG-136), a heteroaromatic polycyclic antibiotic (for example, GSQ1530) or mitomycin C.

In some embodiments, the infectious disease is a bacterial infection or a viral infection. In some embodiments, the hyperproliferative disease is, for example, a tumor, such as a malignant/cancerous tumor, or an autoimmune disease. In some examples, the autoimmune disease is rheumatoid arthritis, lupus, diabetes or multiple sclerosis. In some embodiments, the cancer (or malignant tumor) is a solid tumor or hematogenous cancer. In particular examples, the solid tumor is head and neck cancer, testicular cancer or ovarian cancer. In some examples, the hematogenous cancer is a myeloma or a leukemia.

The pol κ inhibitor of the composition can be any type of molecule that inhibits expression or activity of pol κ. In some embodiments, the pol κ inhibitor is a small molecule inhibitor, an antisense inhibitor or an antibody. In particular examples, the pol κinhibitor is a small molecule inhibitor.

Further provided is a method of identifying an agent that enhances the efficacy of an ICL-inducing agent, comprising screening candidate agents to identify an agent that inhibits activity of pol κ, thereby identifying an agent that enhances the efficacy of an ICL-inducing agent. In some embodiments, the candidate agents are small molecule inhibitors, antisense inhibitors or antibodies. In particular examples, the candidate agents are small molecule inhibitors.

Also provided herein is a screening method to identify DNA polymerase inhibitors, such as inhibitors of DNA pol κ. The method includes mixing a template oligodeoxynucleotide, a primer oligodeoxynucleotide and the DNA polymerase; adding unlabeled dNTPs and a fluorescently-labeled dTTP or dATP; adding a candidate agent; and allowing the reaction to proceed for a sufficient period of time to allow DNA polymerization, wherein a reduction in incorporation of the fluorescently labeled dTTP or dATP in the presence of the inhibitor, relative to incorporation of the fluorescently labeled dTTP or dATP in the absence of the inhibitor, indicates the candidate agent is an agent the inhibits the activity of a DNA polymerase.

In some embodiments, the template oligodeoxynucleotide comprises in the 5' to 3' direction: (i) a 5'-OH, which can be phosphorylated or non-phosphorylated; (ii) a poly dT a poly dA track of about 8 to about 16 nucleotides; (iii) a short segment of nucleotides about 3 to about 7 nucleotides in length, wherein the nucleotides include A, C and G when (ii) is a poly dT track, or the nucleotides include T, C and G when (ii) is a poly dA track; (iv) a primer binding sequence that is complementary to the nucleotide sequence of the primer oligodeoxynucleotide; (v) a linker sequence; (vi) a biotin-conjugated nucleotide; and (vii) 1 to 3 nucleotides at the 3' terminus. The length of the template oligodeoxynucleotide can vary, but is generally about 30 to about 50 nucleotides in length. In some examples, the template oligodeoxynucleotide is about 40 nucleotides in length.

In some examples, the poly dT or poly dA track is about 12 nucleotides in length. When the template oligodeoxynucleotide comprises a poly dT track, the short segment of nucleotides of (iii) includes A, C and G. When the template oligodeoxynucleotide comprises a poly dA track, the short segment of nucleotides of (iii) includes T, C and G.

In some embodiments, the short segment of nucleotides is about 3 to about 7 nucleotides in length. In particular examples, the short segment of nucleotides is about 5 nucleotides in length. In some examples, the short segment of nucleotides comprises a DNA lesion, such as an ICL.

In some embodiments, the primer binding sequence is about 12 to about 24 nucleotides in length, such as about 18 nucleotides in length. In particular examples, the primer binding sequence comprises the nucleotide sequence of SEQ ID NO: 16.

In some embodiments, the linker sequence is a nucleotide sequence. In particular examples, the linker sequence is about 3 to about 10 nucleotides in length. In other embodiments, the linker sequence is an amino acid sequence.

In some embodiments, the primer oligodeoxynucleotide is at least about 95% complementary to the primer binding sequences. In particular examples, the primer oligodeoxynucleotide is 100% complementary to the primer binding sequence.

The DNA polymerase can be any known or yet to be identified DNA polymerase. In some embodiments, the DNA polymerase is polymerase α, β, γ, δ, ν, κ, ι, θ, ϵ or ζ. In particular examples, the DNA polymerase is pol κ.

In some embodiments, the fluorescently labeled dNTP is dATP and the unlabeled dNTPs consist of dTTP, dCTP and dGTP. In other embodiments, the fluorescently labeled dNTP is dTTP or dUTP and the unlabeled dNTPs consist of dATP, dCTP and dGTP.

The candidate agent can be any type of molecule that is suitable for testing in the functional assay described herein. In some embodiments, the candidate agent is a small molecule.

IV. Identification of pol κ Inhibitors

ICL-inducing agents are commonly used as chemotherapeutic or antimicrobial agents because of their ability to damage DNA, thereby rendering the diseased or infected cell susceptible to cell killing mechanisms. It is disclosed herein that human DNA polymerase κ (pol κ) plays an important role in repairing DNA containing ICLs. Repair of ICLs in tumor or infected cells is undesirable. Thus, the present disclosure describes the use of pol κ inhibitors to enhance the efficacy of ICL-inducing agents for the treatment of hyperproliferative, autoimmune or infectious diseases.

DNA polymerases are often up-regulated in tumor cells and it is believed that specific polymerases may contribute to decreased tumor-specific, drug-induced cytotoxicity, as well as increased drug-resistance of surviving tumor cells, leading to secondary tumors that are refractory to additional chemotherapeutic or antimicrobial regimes. Thus, the identification of polymerase inhibitors has therapeutic application as an adjunct therapy in conjunction with combined chemotherapeutic or antimicrobial treatments.

Any suitable type of pol κ inhibitor is contemplated for use as a therapeutic to enhance the efficacy of an ICL-inducing agent. Pol κ inhibitors include, but are not limited to, small molecule inhibitors, nucleic acid molecules, such as antisense compounds, and proteins, such as pol κ-specific antibodies. Methods of identifying polymerase inhibitors are well known in art and are described below.

A. Small Molecule Inhibitors of pol κ

Small molecule inhibitors of pol κ can be identified according to any method known in the art, such as any method that can detect inhibition of pol κ-specific replication or its participation in ICL repair. In some embodiments, the method is a high throughput, automated screen of candidate DNA polymerase inhibitors, such as the assay depicted in FIG. 10. In some examples, the screening assay is based on the inhibition of incorporation of fluorescently labeled nucleotides into duplex DNA as catalyzed by DNA polymerases.

In some examples, the assay involves the use of a template oligodeoxynucleotide having the following features (listed in the 5' to 3' direction):

(i) 5'-OH (which can be phosphorylated or non-phosphorylated);

(ii) a poly dT or poly dA track that serves as the template strand for the incorporation of fluorescently-labeled nucleotides (or other spectroscopically detectable nucleotides);

(iii) a short segment of nucleotides (such as about 3, about 4, about 5, about 6 or about 7 nucleotides) that can be composed of any combination of the three nucleotides that are not found in either the poly dA or poly dT tract at the 5' most end of the oligodeoxynucleotide (for example, if a poly dT is at the 5' end, any combination of A, G, and C can be used in this five-nucleotide segment);

(iv) a primer binding sequence;

(v) a linker sequence that serves as a flexible linkage between the primer-template junction and the site of attachment to the solid matrix support;

(vi) a biotin-conjugated nucleotide near the 3' terminus (such 1 to 5 nucleotides prior to the 3' terminus), which is used to attach the template strand to a solid matrix coated with avidin;

(vii) a short segment of nucleotides (such as about 1 to about 5 nucleotides) for oligodeoxynucleotide synthesis.

Functionally analogous two-component binding systems can be substituted for the biotin-avidin linkage. For example, possible binding partners include, but are not limited to, biotin/streptavidin, antigen/antibody, hapten/antibody, and lectin/carbohydrate. Biotin and avidin analogs and derivatives also can be used as binding partners. The biotin-conjugated nucleotide can optionally be the 3' terminal nucleotide.

The template oligodeoxynucleotide is generally about 30 to about 50 nucleotides in length, such as about 30, about 35, about 40, about 45 or about 50 nucleotides in length. In particular examples, the template oligodeoxynucleotide is 40 nucleotides in length. The poly dA or poly dT track is generally about 8 to about 16 nucleotides in length, such as 8, 9, 10, 11, 12, 13, 14, 15 or 16 nucleotides in length. In particular examples, the poly dA or poly dT track is 12 nucleotides in length. The primer binding sequence is generally about 12 to about 24 nucleotides in length, such as about 12, 13, 14, 15, 16, 17, 18, 19, 20, 21, 22, 23 or 24 nucleotides in length. In particular examples, the primer binding sequence is 18 nucleotides in length. In one example, the primer binding sequence comprises the nucleotide sequence of SEQ ID NO: 16.

The short segment of nucleotides 5' of the primer binding sequence can optionally include a DNA lesion, such as an ICL. This segment of nucleotides is generally about 5 nucleotides in length but can vary as noted above. The primary purpose of this segment of nucleotides is to allow the polymerase to be engaged in DNA synthesis prior to reaching the poly dA or poly dT track where the fluorescently-labeled dNTPs will be incorporated.

The linker sequence can be a nucleotide sequence or a peptide sequence. The length of the linker can vary so long as the linker is a flexible linker between the template and primer. In some cases, the linker is a nucleotide linker of about 3 to about 10 nucleotides in length, such as about 3, 4, 5, 6, 7, 8, 9 or 10 nucleotides in length. In one example, the linker is 5 nucleotides in length.

In some examples, the assay includes mixing approximately equal molar concentrations of the template oligodeoxynucleotide with a primer oligodeoxynucleotide. The primer oligodeoxynucleotide used in the assay is complementary to the primer binding sequence. The primer and template oligodeoxynucleotide are mixed in a solution that is buffered to a physiologically relevant pH using any suitable buffer solution known in the art (such as, for example, 25 mM Tris HCl, Na/K phosphate, or HEPES, and 10 mM $MgCl_2$). The solution is warmed to approximately 12° C. above the melting temperature of the primer/template, and slow cooled to approximately room temperature.

The primer/template is aliquotted into a multi-well plate coated with avidin (or another member of a binding pair). The DNA polymerase to be tested is added to each well, except for pre-selected polymerase-negative wells. The molarity of the polymerase added can be predetermined in small-scale assays. The candidate inhibitor compounds are added to individual wells. In some cases, the plates include known DNA replication inhibitors as controls (such as 20 mM EDTA).

The polymerase reactions are initiated by the addition of the dNTPs (dGTP, dCTP, dATP if the polynucleotide run in the template stand is a poly dA, or dGTP, dCTP, dTTP if the polynucleotide run in the template strand is a poly dT) and a fluorescently labeled dTTP or dATP, as appropriate. The concentration of dNTPs can vary, but is generally at about 10 μM. Similarly, the concentration of fluorescently-labeled dTTP/dATP can vary, but is generally about 1.0 to 10 μM. Candidate inhibitors also are added to the reaction at this step. The temperature of the reaction is raised to about 37° C. and allowed to proceed for a suitable period of time, such as about 30 minutes.

After the reaction is complete, the wells are washed with a buffer that contains a divalent metal chelation compound (such as an EDTA-containing buffer) in order to terminate polymerization and remove any unincorporated fluorescently-labeled dNTP. Buffer is added that is compatible with automated fluorescence detection systems and the plates scanned for the level of fluorescence that has been incorporated opposite the poly dA or poly dT track. If a candidate small molecule inhibitor compound is successful in preventing polymerization, this will be manifested by a lack of or reduced incorporation of the fluorescent dNTP, and thus little or no signal detected.

The assay described above is one example of an assay to identify inhibitors of a DNA polymerase, such as pol κ, but other methods can be used and are contemplated herein. Any template that will support the incorporation and detection of nucleotides by the action of DNA polymerases is suitable for use in a high throughput screen for the identification of inhibitors of DNA polymerases.

In some embodiments, the method further comprises determining whether the candidate pol κ inhibitors are specific to pol κ, or are capable of inhibiting all or multiple DNA polymerases. To identify compounds that inhibit only pol κ, the capacity of the candidate compound to inhibit other DNA polymerases (such as polymerases α, β, γ, δ, ν, ι, θ, ϵ or ζ) can be tested in the assay.

Pol κ-specific small molecule inhibitors identified can then be derivatized. Derivatized compounds can then be further tested in this assay, or another suitable assay, to identify compounds with greater inhibitory properties.

B. Antisense Inhibitors of pol κ

Generally, the principle behind antisense technology is that an antisense compound hybridizes to a target nucleic acid and affects the modulation of gene expression activity, or function, such as transcription, translation or splicing. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide. Antisense oligonucleotides can also be used to modulate gene expression, such as splicing, by occupancy-based inhibition, such as by blocking access to splice sites.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Another type of antisense compound that utilizes the RNAi pathway is microRNA. MicroRNAs are naturally occurring RNAs involved in the regulation of gene expression. However, these compounds can be synthesized to regulate gene expression via the RNAi pathway. Similarly, shRNAs are RNA molecules that form a tight hairpin turn and can be used to silence gene expression via the RNAi pathway. The shRNA hairpin structure is cleaved by the cellular machinery into siRNA.

Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a messenger RNA.

Each of the above-described antisense compounds provides sequence-specific target gene regulation. This sequence-specificity makes antisense compounds effective tools for the selective modulation of a target nucleic acid of interest. In one embodiment, the target nucleic acid is pol κ.

As taught herein, inhibition of pol κ can enhance the efficacy of ICL-inducing agents. Thus, provided are methods of using antisense compounds that target pol κto enhance the efficacy of an ICL-inducing agent. Any type of antisense compound that specifically targets and regulates expression of pol κis contemplated for use with the disclosed methods. Such antisense compounds include single-stranded compounds, such as antisense oligonucleotides, and double-stranded compounds, including compounds with at least partial double-stranded structure, including siRNAs, miRNAs, shRNAs and ribozymes. Methods of designing, preparing and using antisense compounds that specifically target pol κ are within the abilities of one of skill in the art. In some embodiments, pol κ expression is inhibited at least 10%, at least 25%, at least 50%, at least 75%, at least 90%, or at least 95% relative to a control (such as the absence of treatment).

Furthermore, sequences for pol κ are publicly available. An exemplary human nucleotide sequence is deposited under GenBank Accession No. NM_016218 (deposited May 4, 2000). Additional human sequences are publicly available, including, but not limited to the sequences deposited under GenBank Accession Nos. AB209291.1 (deposited Mar. 31, 2005); AF163570.1 (deposited Oct. 16, 1999); AK314610.1 (deposited Jan. 14, 2008); AY769932.1 (deposited Dec. 6, 2004); and BC014955.2 (deposited Oct. 4, 2001). Pol κ nucleotide sequences from other species are also publically available, such as mouse (GenBank Accession No. NM_012048, deposited Jan. 26, 2000); rat (GenBank Accession No. NM_138516, deposited Jun. 7, 2008); and dog (GenBank Accession No. XM_536321, deposited Jan. 4, 2005). Each of the above-listed GenBank Accession sequences is herein incorporated by reference.

Antisense compounds specifically targeting pol κ can be prepared by designing compounds that are complementary to a pol κ nucleotide sequence, particularly the pol κmRNA sequence. Antisense compounds targeting pol κ need not be 100% complementary to pol κ to specifically hybridize and regulate expression the target gene. For example, the antisense compound, or antisense strand of the compound if a double-stranded compound, can be at least 75%, at least 80%, at least 85%, at least 90%, at least 95%, at least 99% or 100% complementary to the selected pol κ nucleic acid sequence. Methods of screening antisense compounds for specificity are well known in the art (see, for example, U.S. Patent Application Publication No. 2003-0228689).

In some examples, the antisense compounds contain one or more modifications to enhance nuclease resistance and/or increase activity of the compound. Modified antisense compounds include those comprising modified bases, modified sugars, modified backbones or non-natural internucleoside linkages. Preparation and use of modified antisense compounds is well known in the art (see, for example, U.S. Patent Application Publication No. 2003-0228689).

Antisense compounds can be delivered to a cell, tissue or organ using any of a number of methods well known in the art. Such methods include, but are not limited to, liposomal-mediated transfection, electroporation and conjugation of the antisense compound to a cell-penetrating peptide. Transfection of antisense compounds generally involves the use of liposomal-mediated transfection reagents, a number of which are commercially available. Methods for transfection and electroporation of nucleic acids, including antisense compounds, are well known in the art (see, for example, U.S. Pat. Nos. 7,307,069 and 7,288,530; Pretchtel et al., *J. Immunol. Methods* 311(1-2):139-52, 2006; Ghartey-Tagoe et al., *Int. J. Pharm.* 315(1-2):122-133, 2006). Antisense compounds are administered to a subject in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure, which are discussed in further detail below.

C. Antibodies Specific for pol κ

A pol κ polypeptide or a fragment or conservative variant thereof can be used to produce antibodies which are immunoreactive or specifically bind to an epitope of pol κ. Polyclonal antibodies, antibodies which consist essentially of pooled monoclonal antibodies with different epitopic specificities, as well as distinct monoclonal antibody preparations are included.

The preparation of polyclonal antibodies is well known to those skilled in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992).

The preparation of monoclonal antibodies likewise is conventional (see, for example, Kohler & Milstein, *Nature* 256: 495, 1975; Coligan et al., sections 2.5.1-2.6.7; and Harlow et al. in: *Antibodies: a Laboratory Manual*, page 726, Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465, 1991; and Losman et al., *Int. J. Cancer* 46:310, 1990.

Alternatively, an antibody that specifically binds a pol κ polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, $F(ab')_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Natl. Acad. Sci. U.S.A.* 69:2659, 1972). Alternatively, the variable chains can be linked by an intermolecular disulfide bond or cross-linked by chemicals such as glutaraldehyde (see, for example, Sandhu, *Crit. Rev. Biotech.* 12:437, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

V. Methods of Use of pol k Inhibitors

Chemotherapeutic and antimicrobial protocols for the treatment of cancers or microbial infections frequently use chemical agents that kill cells by virtue of their ability to covalently crosslink complementary strands of DNA together, referred to as an interstrand crosslink (ICL). The mechanism by which ICL agents kill cells is to prevent DNA strand separation during essential cellular processes, such as DNA replication, RNA transcription and homologous recombination. In order for a cell to survive following ICL formation, DNA repair processes must recognize these lesions and initiate and complete the removal of the ICL. It is disclosed herein that human DNA pol κ is responsible for catalyzing translesion synthesis of DNA containing an incised ICL. Thus, pol κ is essential for restoring ICL-containing DNAs to a replication, transcription and homologous recombination competent state. Such activity would limit the effectiveness of ICL-inducing chemotherapeutic and antimicrobial agents to kill their target cells (e.g., cancer cells or infected cells). Therefore, the disclosed methods inhibit the activity of pol κ in target cells to enhance the efficacy of ICL-inducing agents.

Provided herein is a method of enhancing the efficacy of an ICL-inducing agent in a subject, including selecting a subject in need of treatment and administering to the subject an inhibitor of pol κ. Also provided is a method of treating a subject having a hyperproliferative disorder, an autoimmune disease or an infectious disease comprising administering to the subject a chemotherapeutic or antimicrobial agent and an inhibitor of pol κ.

Pol κ inhibitors can be administered in combination with any ICL-inducing agent for the treatment of any type of hyperproliferative disorder, autoimmune disease or infectious disease. For example, hyperproliferative disorders include tumors, such as benign tumors or malignant tumors. Malignant tumors (also referred to as cancer) include both solid tumors and hematogenous cancers. The pol κ inhibitor can be administered with an ICL-inducing agent, following administration of the ICL-inducing agent, or both. Combination treatment can be achieved either by concurrent administration of the agents together, or sequential administration in sufficient close temporal proximity for the pol κ inhibitor to enhance the effect of the ICL-inducing agent. The pol κ inhibitor can be administered before or after the ICL-inducing agent.

As one example, a subject diagnosed with head and neck squamous cell carcinoma is administered a chemotherapeutic agent, such as cisplatin (Cooper et al., *N. Engl. J. Med.* 350 (19):1937-1944, 2004). A pol κinhibitor can be administered in combination with the chemotherapeutic (ICL-inducing) agent to enhance the efficacy of chemotherapy. A similar treatment regimen can be used for patients with other types of cancer that respond to cisplatin therapy, such as testicular cancer, ovarian cancer or other reproductive cancers.

In another example, a subject diagnosed with multiple myeloma is administered a chemotherapeutic (ICL-inducing) agent, such as melphalan. A pol κ inhibitor is administered in combination with the ICL-inducing agent to enhance the efficacy of chemotherapy. A similar treatment regimen can be used for patients with other types of cancer that respond to melphalan therapy, such as ovarian cancer and colorectal cancer.

In another example, a subject diagnosed with a lymphoma is administered an ICL-inducing agent, such as CYTOXAN™. A pol κ inhibitor is administered in combination with CYTOXAN™ to enhance the efficacy of chemotherapy. The lymphoma can be any type of lymphoma that responds to treatment with CYTOXAN™, such as Hodgkin's lymphoma or non-Hodgkin's lymphoma. A similar treatment regimen can be used for patients with other types of cancer that respond to CYTOXAN™ therapy, such as breast cancer, multiple myeloma, retinoblastoma, ovarian cancer, neuroblastoma and leukemia (including acute lymphoblastic leukemia, acute myeloid leukemia, chronic lymphocytic leukemia and chronic myelogenous leukemia).

In another example, a subject in need of bone marrow transplantation/conditioning for the treatment of chronic myelogenous leukemia or chronic lymphocytic leukemia is administered busulfan. A pol κ inhibitor is administered in combination with busulfan to improve therapeutic outcome.

In another example, a subject diagnosed with an autoimmune disease, such as rheumatoid arthritis is administered a chemotherapeutic agent (such as cyclophosphamide) in combination with a pol κ inhibitor.

In each example, the pol κ inhibitor can be administered in one dose, such as with the first dose of chemotherapeutic agent, or can be administered in several doses, such as with each dose of chemotherapy. The pol κ inhibitor can further be administered between doses and/or after one or more doses of chemotherapy.

Pol κ inhibitors can also be used for local or topical applications. For example, an ICL-inducing agent and a pol κ inhibitor can be applied topically or locally to an infected area, such as a lesion in the skin, or the eye (for example, the conjunctiva) or via an abscess cavity. For example, a pol κ inhibitor can be applied with an ICL-inducing agent such as mitomycin C to an intra-operative bleb formed during glaucoma surgery to maintain patency of the bleb (Giampani et al., *Clinics* 63(4):421-6, 2008; Nobel et al., *Can. J. Ophthalmol.* 42:89-94, 2007). In another example, an ICL-inducing agent (such as mitomycin C) is infused into the bladder to treat bladder tumors (Shen et al., *Pharm. Res.* 25(7):1500-1510, 2008). A pol κ inhibitor is also administered to enhance the efficacy of the ICL-inducing agent.

Pol κ inhibitors can also be used for the treatment of infectious diseases, such as infection by *Staphylococcus aureas*, including methicillin-resistant *Staphylococcus aureas* (known as MRSA). For example, a subject diagnosed with a *Staphylococcus aureas* infection is administered an ICL-inducing agent, such as a pyrrolobenzodiazepine (for example, SJG-136). A pol κ inhibitor is also administered to enhance the efficacy of the ICL-inducing agent.

VI. Administration of pol k Inhibitors

Pol κ inhibitors are preferably administered to a subject in a pharmaceutically acceptable carrier or diluent. The choice of pharmaceutically acceptable carrier will depend on a variety of factors, including the type of inhibitor, route of administration, and the disease to be treated. An inhibitor of pol κ can be administered using any suitable route, including, for example, parenteral, oral or topical.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Administration can be accomplished by single or multiple doses. The dose required will vary from subject to subject depending on the species, age, weight and general condition of the subject, the particular type of pol κ inhibitor being used (for example, small molecule, antisense compound or antibody) and its mode of administration. An appropriate dose can be determined by one of ordinary skill in the art using only routine experimentation. If administered in multiple doses, the time between delivery of each dose can vary between days, weeks, months and years.

The following examples are provided to illustrate certain particular features and/or embodiments. These examples should not be construed to limit the disclosure to the particular features or embodiments described.

EXAMPLES

Example 1

Materials and Methods

Preparation of Oligodeoxynucleotides Containing Site-Specific ICLs

Modified oligodeoxynucleotides were synthesized on a PerSeptive Biosystems™ Model 8909 DNA synthesizer using Expedite reagents with the standard synthetic protocol on a 1-μmol scale. The 2-fluoro-2'-deoxyinosine-modified oligodeoxynucleotide was prepared using a standard DNA synthesizer cycle with (p-tert-butylphenoxy)acetyl-protected phosphoramidites. The modified oligodeoxynucleotides were cleaved from the solid support and the exocyclic amino groups were deprotected in a single step using 0.1 M aq NaOH.

Preparation of Oligodeoxynucleotides

Figure 6:
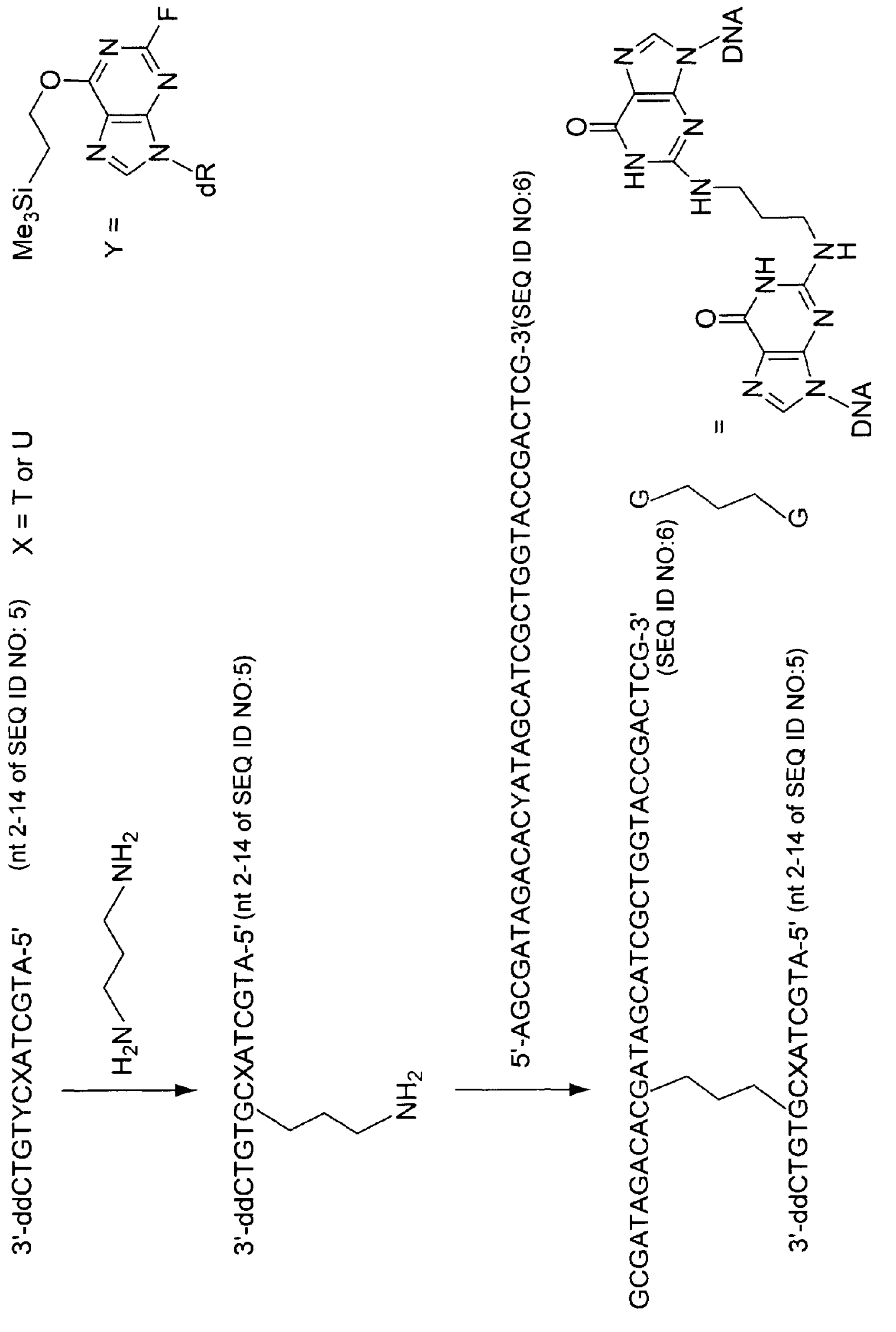
FIG. 6 is a schematic of the experimental procedure for the sequential synthesis steps of ICL formation.

Unmodified oligodeoxynucleotides were synthesized according to standard procedures. Modified oligodeoxynucleotides were synthesized as previously described (Dooley et al., *J. Am. Chem. Soc.* 123:1730-1739, 2001; and Dooley et al., *J. Am. Chem. Soc.* 125:62-72, 2003). The experimental procedure that summarizes the sequential synthesis steps for ICL formation is shown in FIG. 6. The 2-fluoro-2'-inosine modified oligodeoxynucleotide was mixed in a plastic test tube with diisopropylethylamine, 1,3-diaminopropane, and DMSO. The reaction mixture was stirred at 60° C. and the reaction was complete in 1 hour; HPLC analysis showed disappearance of the starting material. The solvents were removed in vacuo by centrifugal evaporation and the residue was treated with 5% acetic acid for 2 hours at room temperature. After neutralization, the reaction mixture was purified by HPLC. The oligodeoxynucleotide was dried on a lyophilizer, then dissolved in 0.1 M NaOH and repurified by ion-exchange chromatography (Bio-Rad ECONO-PAC® High Q) using a gradient of 0.1 M NaOH to 0.1 M NaOH containing NaC1 (0.6 M) to remove unreacted 1,3-diaminopropane. The eluant was neutralized with 20% acetic acid and desalted to give of a $N^2$-(3-aminopropyl)-dG modified oligonucleotide.

The $N^2$-(3-aminopropyl)-dG adducted oligodeoxynucleotide synthesized above, and the complementary oligodeoxynucleotide containing 2-fluoro-2'-deoxyinosine base were mixed in a plastic test tube with 0.05 M sodium borate buffer (pH 9). The reaction mixture was stirred at 40° C. and the progress of the reaction was followed by HPLC. After the reaction was complete, the mixture was treated with 5% acetic acid for 1 hour at room temperature, and was then purified by HPLC and desalted as described above. The crosslinked product was also characterized by MALDI-TOF-MS, enzyme digestion, and capillary gel electrophoresis. The presence of the crosslink was confirmed by enzymatic digestion and observation of dG-$(CH_2)_3$-dG by HPLC. The crosslinked nucleoside was previously synthesized and characterized (Kozekov et al., *Chem. Res. Toxicol.* 14:1482-1485, 2001; Kozekov et al., *J. Am. Chem. Soc.* 125:50-61, 2003).

a.

(SEQ ID NO: 6)

5'-AGC GAT AGA CAC $G^{(CH2)3NH2}$AT AGC ATC GCT GGT ACC GAC TCG-3'

Yield: 68%

MALDI-TOF MS: calculated for $[M-H]^-$ 11129.9, found 11132.1 b. ICL1

(SEQ ID NO: 5)

3'-ddCT GTG CTA TCG TAG-5'

(SEQ ID NO: 6)

5'-AGC GAT AGA CAC GAT AGC ATC GCT GGT ACC GAC TCG-3'

G,G=G-$(CH_2)_3$-G

Yield: 51%; reaction time 4 day; CGE 92.9%

MALDI-TOF MS: calculated for $[M-H]^-$ 15373.2, found 15372.4 c. Uracil-Containing Precursor of ICL2

(nucleotides 2-14 of SEQ ID NO: 5)

3'-ddCT GTG CUA TCG TA-5'

(SEQ ID NO: 6)

5'-AGC GAT AGA CAC GAT AGC ATC GCT GGT ACC GAC TCG-3'

(G,G=G-$(CH_2)_3$-G)

Yield: 45%; reaction time 3 day; CGE 90.8%

MALDI-TOF MS: calculated for $[M-H]^-$ 15029.9, found 15031.2 d.

(nucleotides 1-10 of SEQ ID NO: 5)

3'-gl- $G^{(CH2)3NH2}$CT ATC GTA G-5'

Yield: 78%

MALDI-TOF MS: calculated for $[M-H]^-$ 3252.6, found 3252.3 e. ICL3

(nucleotides 1-10 of SEQ ID NO: 5)

3'-gl- G CTA TCG TAG-5'

(SEQ ID NO: 6)

5'-AGC GAT AGA CAC GAT AGC ATC GCT GGT ACC GAC TCG-3'

G,G=G-$(CH_2)_3$-G

Yield: 31%; reaction time 10 day; CGE 96.9%

MALDI-TOF MS: calculated for $[M-H]^-$ 14315.4, found 14314.8 f.

(nucleotides 2-10 of SEQ ID NO: 5)

3'-gl- $G^{(CH^2)3NH^2}$C UAT CGT A-5'

Yield: 74%

MALDI-TOF MS: calculated for $[M-H]^-$ 12909.5, found 2909.4 g. Uracil-Containing Precursor of ICL4.

(nucleotides 2-10 of SEQ ID NO: 5)

3'-gl-G CUA TCG TA-5'

(SEQ ID NO: 6)

5'-AGC GAT AGA CAC GAT AGC ATC GCT GGT ACC GAC TCG-3'

G,G=G-$(CH_2)_3$-G

Yield: 28%; reaction time 10 day; CGE 99.1%

MALDI-TOF MS: calculated for $[M-H]^-$ 13972.2, found 13969.9 h.

3' CCT GA G$^{(CH_2)_3NH_2}$CGA TCG 5' (SEQ ID NO: 1)

Yield: 69%

MALDI-TOF MS: calculated for $[M-H]^-$ 3701.7, found 3701.5 i. CpG ICL (SEQ ID NO: 1)
3'-CCTGAGCGATCG-5'

(SEQ ID NO: 2)
5'-CCTGCAAGCGATGGACTCGCTAGCATCGCTGGTACC-3'

G,G=G-$(CH_2)_3$-G

Yield: 42%; CGE 99.5%

MALDI-TOF MS: calculated for $[M-H]^-$ 14701.6, found 14702.8

J.

3' CCT AGC G$^{(CH_2)_3NH_2}$AG TCG 5' (SEQ ID NO: 3)

Yield: 65%

MALDI-TOF MS: calculated for $[M-H]^-$ 3701.7, found 3701.6 k. GpC ICL (SEQ ID NO: 3)
3'-CCTAGCGAGTCG-5'

(SEQ ID NO: 4)
5'-CCTGCAAGCGATGGATCGCTCAGCATCGCTGGTACC-3

G,G=G-$(CH_2)_3$-G

Yield: 10%; CGE 94.5%

MALDI-TOF MS: calculated for $[M-H]^-$ 14701.6, found 14706.6

HPLC Separations

Purifications and analyses were performed on a Beckman (Beckman Coulter) HPLC system (32 KARAT™ software version 7.0, pump module 125) with a diode array UV detector (module 168) monitoring at 260 nm. A Waters YMC ODS-AQ column (250 mm ×10 mm i.d., 5 mL/min) was used to purify oligonucleotides using 0.1 M aqueous ammonium formate and acetonitrile as the mobile phase. The adduction reactions were monitored with a Waters YMC ODS-AQ column (250 mm×4.6 mm i.d., 1.5 mL/min) using 0.1 M aqueous ammonium formate and acetontitrile as the mobile phase. Nucleoside analyses from enzymatic digestions were performed with a Waters YMC ODS-AQ column (250 mm×4.6 mm i.d., 1.5 mL/min) using water and acetontitrile as the mobile phase. In all cases, the following HPLC gradient was used: 1-10% acetonitrile over 15 minutes, 10-20% acetonitrile over 5 min, hold for 5 min, 100% acetonitrile over 3 minutes, hold for 2 minutes, and then to 1% acetonitrile over 3 minutes.

PAGE Separation

After initial HPLC purification, the crosslinked oligodeoxynucleotides were further purified by polyacrylamide gel electrophoresis (PAGE) on a model SE 620 gel tank (Hoefer Scientific Instruments) filled with 1×TBE buffer using an EC4000P Series 90 Programmable power supply (E-C Apparatus Corporation) set at a constant 1200 volts. PAGE purification was run on a 15% acrylamide (w/v) (from a 19:1 acrylamide:bisacrylamide solution, BioRad) and 7M urea gel. Imaging of the gel was accomplished by UV visualization (254 nM). Following separation, bands were excised and the oligodeoxynucleotides were eluted from crushed gel overnight in 0.05 M triethylammonium acetate (TEAA) buffer (pH 7.0) followed by Millipore water desalting system.

Capillary Gel Electrophoresis (CGE)

Electrophoretic analyses were carried out using a Beckman P/ACE™ MDQ instrument system (using 32 KARAT™ software, version 5.0) monitored at 260 nm on a 31.2 cm×100 μm eCAP capillary with samples applied at 10 kV and run at 9 kV. The capillary was packed with their 100-R gel (for ss-DNA) using the Tris-borate buffer system containing 7 M urea.

Mass Spectrometry

MALDI-TOF mass spectra (negative ion) of modified oligodeoxynucleotides were obtained on a Voyager Elite DE instrument (PerSeptive Biosystems) at the Vanderbilt Mass Spectrometry Facility using a 3-hydroxypicolinic acid matrix containing ammonium hydrogen citrate (7 mg/mL) to suppress multiple sodium and potassium adducts (see Table 1).

TABLE 1

Characterizationof ICL-containing oligodeoxynucleotides by mass spectrometry

| Oligodeoxynucleotide | Calculated | Observed | Error (%) |
|---|---|---|---|
| ICL1 | 15373.2 | 15372.4 | 0.005 |
| Uracil-containing precursor of ICL2 | 15029.9 | 15031.2 | 0.009 |
| ICL3 | 14315.4 | 14314.8 | 0.004 |
| Uracil-containing precursor of ICL4 | 13972.2 | 13969.9 | 0.016 |
| CpG ICL | 14701.6 | 14702.8 | 0.008 |
| CpG ICL | 14701.3 | 14706.6 | 0.034 |

Enzymatic Hydrolysis

Enzymatic hydrolysis was carried out in one step. Oligonucleotide (0.2-0.5 $A_{260}$ units) was dissolved in 30 μL buffer (pH 7.0, 10 mM Tris-HCl, 10 mM $MgCl_2$) and incubated with DNase I (8 units, Promega), snake venom phosphodiesterase I (0.02 units, Sigma), and alkaline phosphatase (1.7 units, Sigma) at 37° C. for 24 hours. The mixture was analyzed by reverse phase HPLC. Adducted nucleosides were identified by comparison with authentic samples based on retention times, co-injection, and ultraviolet spectra.

Preparation of ICL2 and ICL4

To obtain ICL2 and ICL4, uracil-containing precursor oligodeoxynucleotides (160 pmol) were sequentially treated with 8 units uracil DNA glycosylase (New England BioLabs) and T4-pyrimidine dimer glycosylase/abasic site lyase (1 μg), purified as described by Jaruga et al. (*Photochem. Photobiol.* 75:85-91, 2002). Reactions were performed at 37° C. for 1 hour. Following heat-inactivation of proteins at 95° C. for 10 minutes, oligodeoxynucleotides were purified using P-6 Bio-Spin columns To test for completeness of conversion of the precursor oligodeoxynucleotides into products, DNA probes were taken before and after the treatment, radioactively labeled with T4 polynucleotide kinase in the presence of [$\gamma$-$^{32}$]-ATP, and subjected to the gel electrophoresis under denaturing conditions.

Cell Lines

COS-7 cells were purchased from the American Type Culture Collection. GM639 human fibroblasts were obtained from NIGMS Human Genetic Cell Repository.

Mutagenesis Assays

Mutagenesis assays were performed using a previously developed pMS2 shuttle vector/COS-7 system (Moriya, *Proc. Natl. Acad. Sci. U.S.A.* 90:1122-1126, 1993). In its single-stranded form, the pMS2 vector contains a hairpin loop with an internal EcoRV restriction site. Incorporation of control non-damaged oligodeoxynucleotides into this site was accomplished in the presence of a scaffold DNA according to a published method (Kanuri et al., *J. Biol. Chem.* 277:18257-18265, 2002). To create a single-stranded pMS2 containing site-specific interstrand crosslink, the procedure was modified as described below.

Oligodeoxynucleotides containing a model acrolein-derived site-specific interstrand crosslink (FIG. 1A and FIG. 1B) were designed in such a way that peripheral regions of the longer strands (36-mer) were complementary to the vector sequences immediately adjacent to the EcoRV site. A circular single-stranded pMS2 vector (approximately 15 pmol) was digested with 40 units of EcoRV (New England BioLabs) for 3 hours at 37° C. to generate a linear DNA. 5'-phosphorylated crosslinked inserts (60 pmol) were added to the linear single-stranded pMS2 (15 pmol), and ligated using 60 units of T4 DNA ligase (New England BioLabs) for 48 hours at 4° C. To obtain double-stranded pMS2 vectors, the 36-mer strand of the crosslink or the scaffold oligodeoxynucleotide in control DNA was extended using 5 units of T4 DNA polymerase (New England BioLabs) and 1 mM dNTPs at 37° C. for 1 hour. A newly-synthesized strand was concomitantly sealed using 5 units of T4 DNA ligase (New England BioLabs). The creation of double-stranded pMS2 was verified by PstI (New England BioLabs) digestion.

Transfection of pMS2 vector into COS-7 cells, isolation of progeny DNA, selection of individual clones by *E. coli* transformation, and differential hybridization analyses were performed as previously described (Moriya, *Proc. Natl. Acad. Sci. U.S.A.* 90:1122-1126, 1993; Kanuri et al., *J. Biol. Chem.* 277:18257-18265, 2002).

DNA Polymerase Bypass Assays

Preparations of primer/template DNA substrates were performed as previously described (Minko et al., *J. Biol. Chem.* 278:784-790, 2003). Human recombinant pol κ and *S. cerevisiae* recombinant Rev1 and pol ζ were obtained from Enzymax. Prior to polymerase bypass assays, polymerase preparations were tested for contaminating exonucleolytic activities. Primer/template non-damaged DNA substrate (5 nM) was incubated with each individual polymerase (2 nM) under conditions identical to polymerase reactions, but in the absence of dNTPs. No primer degradation was observed after a 30-minute incubation at 37° C. Polymerase bypass assays were performed using 5 nM primer/template DNA substrates in the presence of 25 mM sodium phosphate (pH 7.5), 5 mM $MgCl_2$, 10% glycerol, 10 mM NaCl, 0.1 mg/ml bovine serum albumin, and 5 mM dithiothreitol at 37° C. Primer extensions were conducted with 100 μM dNTPs. Single nucleotide incorporations were performed with 20 μM of an individual dNTP.

Prior to reactions using a combination of pol ζ and Rev 1 proteins, pol ζ alone or in a mixture with Rev1 was pre-incubated overnight on ice in the presence of 25 mM sodium phosphate (pH 7.5), 10% glycerol, 0.1 mg/ml bovine serum albumin, and 5 mM dithiothreitol. Polymerase reactions were terminated by the addition of an equal volume of a solution consisting of 95% formamide, 20 mM EDTA, 0.2% (w/v) bromophenol blue, and 0.2% xylene cyanol. Products were resolved through a 15% denaturing polyacrylamide gel in the presence of 8 M urea and visualized using a PHOSPHORIMAGER™ screen (GE Healthcare).

Steady-state kinetic analyses were performed according to a standard procedure (Creighton et al., *Methods Enzymol.* 262:232-256, 1995). Briefly, reactions were conducted under the same conditions as single nucleotide incorporation assays except that the primer/template DNA concentration was 10 nM, dCTP or dGTP were used at various concentrations, reactions were conducted at 22° C., and polymerase concentrations and incubation times were adjusted not to exceed 25% of the product formation. Quantitative analyses were performed using Image-Quant 5.2 software (Molecular Dynamics). Rates of dNTP incorporation were plotted as a function of dNTP concentration and the data were analyzed using KALEIDAGRAPH™ 3.6 software (Synergy Software). The $k_{cat}$ and $K_m$ parameters with their error values were obtained from the best fit of the data to the Michaelis-Menten equation: $v_{obs}=k_{cat}[E][dNTP]/(K_m+[dNTP])$. Relative efficiencies were calculated as a ratio of the efficiency of reaction using ICL template to the efficiency measured for undamaged template.

Transfection of GM639 Cells siRNA transfections were performed as previously described (Bruun et al., *DNA Repair* (*Amst*) 2:1007-1013, 2003). Briefly, cells were transfected with SMARTPOOL™ siRNA (Dharmacon) specific to pol κ diluted to 0.30 μM, or were mock transfected. The final transfection volumes were 1.0 mL for a T25 flask and 3.2 mL for a 100 mm dish.

Cell Survival Assays

Twenty four hours after siRNA transfection, cells were plated on 100 mm dishes to a density of 300 cells per dish in alpha-MEM medium, treated with MMC (Sigma), and allowed to grow for 10 days. Cells were fixed in a solution of 50% MeOH and 1% new methylene blue (Sigma), and surviving colonies were counted.

Chromosome Stability

Twenty four hours after siRNA transfection, cells were treated with MMC (40 ng/mL), incubated for 48 hours, and harvested as described (Bruun et al., *DNA Repair* (*Amst*) 2:1007-1013, 2003). Slides were stained with Wright's stain, and 50 metaphases from each culture were scored for radial formation.

Quantification of pol κ mRNA

Cells were harvested 24 hours after siRNA transfection. RNA was stabilized using RNALATER™ (Ambion), extracted using the RNEASY™ Mini Kit (Qiagen), and quantified. Reverse transcription was performed with the High Capacity cDNA Reverse Transcription Kit (Applied Biosystems) using 1 μg of starting RNA material. Real-time quantitative PCR was performed using the ICYCLER IQ™ Detection System (BioRad) with 10 ng of starting cDNA material using the TAQMAN™. Gene Expression Assay specific to pol κ (Applied Biosystems). Primers specific to the housekeeping gene β-actin (Applied Biosystems) were used for internal control. Each sample was tested in triplicate. An amplification plot was created for each sample. Threshold values were calculated from the amplification plots correlating to the cycle number where florescence was detected above a calculated threshold. The mRNA concentrations for each sample were calculated with the Ct value and were normalized against β-actin expression. Negative controls for each primer were included in each experiment.

Statistical Analysis

The means, standard errors of the means, and P values from the Student t-tests were obtained using KALEIDAGRAPH™ 3.6 software (Synergy Software).

Example 3

Mutagenic Properties of Model Acrolein-Derived $N^2$-$N^2$-guanine ICLs

Previous studies have established that in human cells, crotonaldehyde-mediated $N^2$-$N^2$-guanine ICLs were repaired mostly (>94%) in an error-free manner (Liu et al., *Biochemistry* 45:12898-12905, 2006). Since acrolein-mediated ICLs are structurally similar to crotonaldehyde-mediated ICLs, it is possible that model acrolein-derived $N^2$-$N^2$-guanine ICL (FIG. 1A) would not be highly mutagenic when plasmid vectors containing this lesion were replicated in mammalian cells. In order to test this, oligodeoxynucleotides were constructed to contain a site-specific ICL in either CpG or GpC sequence contexts (FIG. 1B) and engineered into a double-stranded DNA shuttle vector (pMS2). The vector was replicated in COS-7 cells, and progeny DNAs were analyzed to determine frequency and types of mutations. In both the CpG and GpC sequence contexts, the mutation frequencies were very low, 3.0% and 3.2%, respectively (Table 2).

TABLE 2

Mutations generated during replication of site-specifically modified pMS2 vector in COS-7 cells

| DNA modification | Colonies scored | # Single base substitutions G to A | G to C | G to T | Deletions | Frequency of mutations (%) |
|---|---|---|---|---|---|---|
| Undamaged | 315 | 0 | 0 | 0 | 0 | 0 |
| ICL in GpC | 342 | 4 | 1 | 1 | 5 | 3.2 |
| ICL in CpG | 66 | 0 | 0 | 2 | 0 | 3.0 |

Mutations were single base substitutions as well as deletions that generally began at, or one nucleotide downstream of, the ICL and extended <15 nucleotides. Thus, during replication of plasmids containing model acrolein-mediated $N^2$-$N^2$-guanine ICLs, a majority of bypass events were error-free in COS-7 cells. In the CpG sequence context, the base substitutions were G to T transversions, a result that is in agreement with previously reported data on mutagenic properties of crotonaldehyde-mediated (Liu et al., *Biochemistry* 45:12898-12905, 2006) and MMC-induced $N^2$-$N^2$-guanine ICLs (Zheng et al., *Mol. Cell. Biol.* 23:754-761, 2003).

Design and Construction of DNA Substrates for Replication Bypass Assays

In order to investigate DNA polymerase bypass of ICLs, DNAs containing acrolein-derived $N^2$-$N^2$ guanine crosslinks (FIG. 1A) were designed to mimic potential intermediates in the processing of ICLs (FIG. 1C). Crosslinked DNA 1 (ICL1) represents a model of the DNA product following dual incision around the ICL site, while ICL2, ICL3, and ICL4 represent the products of either exonucleolytic or endonucleolytic processing of the 5' or 3' end or both, respectively, up to, but not including the crosslink. The non-damaged ND2 substrate was designed to mimic a structure encountered by a polymerase in ICLs 1 and 3, but contains no damage.

Endonucleolytic processing of ICL-containing DNAs has been addressed in a number of biochemical studies using either preparations of chromatin-associated proteins (Kumaresan et al., *J. Biol. Chem.* 270:30709-30716, 1995) or the purified XPF-ERCC1 complex (Kuraoka et al., *J. Biol. Chem.* 275:26632-26636, 2000; Fisher et al., *J. Biol. Chem.* 283:1275-1281, 2008), a structure-specific endonuclease that is essential for ICL repair (Wu et al., *Cancer Res.* 64:3940-3948, 2004, De Silva et al., *Mol. Cell. Biol.* 20:7980-7990, 2000). In these investigations, a variety of structurally diverse substrates were utilized, including splayed, Y-shaped, and fully duplex DNAs. Incisions were commonly observed both 5' and 3' to the ICL sites, suggesting generation of excision products (i.e. the DNA fragments that presumably remain connected to the opposite strand). The estimated sizes of these DNA fragments were in a range from 4 to 17 deoxynucleotides (Kumaresan et al., *J. Biol. Chem.* 270:30709-30716, 1995; Kuraoka et al., *J. Biol. Chem.* 275:26632-26636, 2000; Fisher et al., *J. Biol. Chem.* 283:1275-1281, 2008). Thus, the ICL1 substrate in which a 12-mer oligodeoxynucleotide is covalently attached to the longer strand, represents a reasonable model for a dually incised ICL-containing DNA.

Recently, significant progress has been made in structural characterization of TLS polymerases. Although TLS polymerases appear to have relatively spacious active sites (Prakash et al., *Annu. Rev. Biochem.* 74:317-353, 2005; Uljon et al., *Structure* 12:1395-1404, 2004; Nair et al., *Science* 309:2219-2222, 2005; Lone et al., *Mol. Cell.* 25, 601-614, 2007; Broyde et al., *Chem. Res. Toxicol.* 21:45-52, 2008), it is unlikely that a dually incised ICL-containing DNA could be accommodated there, properly positioned, and utilized as template. Thus, remodeling of the overall DNA structure and/or processing of the incised DNA fragment are thought to be required prior to TLS. In this regard, it is significant that the XPF-ERCC1 complex and its yeast counterpart, Rad1-Rad10, both posses the 3' to 5' exonucleolytic activity (Guzder et al., *Genes Dev.* 18:2283-2291, 2004; Mu et al., *Mol. Cell. Biol.* 20:2446-2454, 2000). Specifically, it has been shown that Rad1-Rad10 degrades DNA from the 3' end, releasing products 3 to 6 nucleotides in length (Guzder et al., *Genes Dev.* 18:2283-2291, 2004). Thus, it is possible that following the endonucleolytic cleavage 3' to the ICL site, incised DNA will be further processed exonucleolytically by the XPF-ERCC1 (Rad1-Rad10) complex. Such an action could create the structure as in ICL2. ICL3 represents the product of exonucleolytic processing of the 5' of the excised DNA fragment. The potential candidate to perform this reaction would be Snml, which has a demonstrated 5' to 3' exonuclease activity (39,40) and in yeast, is critical for ICL repair (Henriques and Moustacchi, *Genetics* 95:273-288, 1980; Grossmann et al., *Mutat. Res.* 487:73-83, 2001; Wu et al., *Cancer Res.* 64:3940-3948, 2004). However, alternative enzymes could also play a role in the processing of ICL-containing DNA to yield structures that would favor the replication bypass. These may include alternative exonucleases, replicative and repair helicases, flap endonucleases, and exonuclease activities associated with helicases and polymerases.

Primer oligodeoxynucleotides (FIG. 1D) were designed to perform DNA syntheses under running start (−10 primer) or standing start (−1 primer) conditions, or to test for extension from a nucleotide that is opposite to the crosslinked G (0 primers).

Example 4

Replication Bypass of Model Acrolein-Derived $N^2$-$N^2$-Guanine ICLs by Human pol κ

Prior findings demonstrated that pol κ could carry out TLS past various bulky $N^2$-guanine adducts and was critical in limiting mutagenesis from these lesions (Zhang et al., *DNA Repair* (Amst) 1:559-569, 2002; Ogi et al., *Proc. Natl. Acad. Sci. U.S.A.* 99:15548-15553, 2002; Avkin et al., *J. Biol. Chem.* 279:53298-53305, 2004; Choi et al., *J. Biol. Chem.* 281, 21062-21072, 2006; Jarosz et al., *Nature* 439:225-228, 2006). Since in the model ICL described herein the linkage is mediated through the exocyclic amino group of guanines, it was hypothesized that pol κ may catalyze replication bypass of this lesion. A $^{32}P$-labeled oligodeoxynucleotide primer (−10 primer, FIG. 1D) was hybridized with template DNAs and primer extension reactions were conducted using human pol κ (FIG. 2A). A processive DNA synthesis by pol κ was observed on both undamaged substrates with a partial inhibition of replication at initiation of strand displacement synthesis using ND2. Analyses of primer extension reactions on crosslinked substrates in which the four nucleotides that were 3' to the crosslink had been removed (ICL3 and ICL4) revealed that pol κ could also catalyze TLS past the crosslinked site. In 45 minute reactions, approximately 10 and 74% of primers were extended beyond the crosslinked guanine in ICL3 and ICL4, respectively, versus approximately 79% of primers extended beyond the corresponding guanine in ND1. Additionally, pol κ was able to catalyze limited synthesis past the crosslink in ICL2 with about 2% of primers extended beyond the lesion.

Figure 2B:
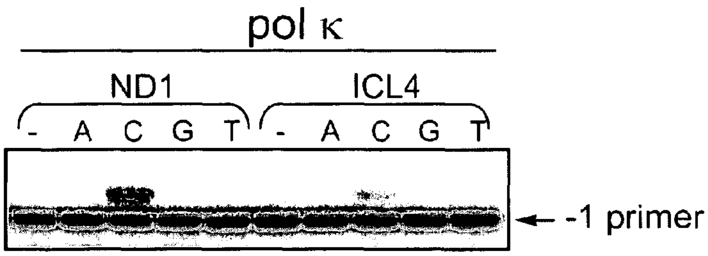

In order to identify nucleotide(s) that pol κ inserts opposite the crosslinked G, single nucleotide incorporation assays were conducted using the −1 primer (FIG. 2B). Similar to results obtained for ND1 substrate, using the ICL4 template, extension products were detected only in reactions supplemented with dCTP, but not the other dNTPs. The catalytic efficiency ($k_{cat}/K_m$) of dCTP incorporation by pol κ opposite control G versus the crosslinked G revealed a 35-fold decrease, while efficiency of extension from a C opposite the lesion was reduced approximately 7-fold (Table 3). Overall, these data indicate that pol κ can accurately bypass $N^2$-$N^2$ guanine ICLs, representing the first biochemical evidence for TLS by any DNA polymerase past any ICL.

TABLE 3

Steady-state kinetic parameters for ICL bypass by pol κ

| Primer | DNA substrate | dNTP | $k_{cat}$ ($min^{-1}$) | $K_m$ (μM) | $k_{cat}/K_m$ ($\mu M^{-1}min^{-1}$) | Relative efficiency |
|---|---|---|---|---|---|---|
| −1 | ND1 | dCTP | 0.19 ± 0.01 | 22 ± 2 | $8.6 \times 10^{-3}$ | 1 |
| −1 | ICL4 | dCTP | 0.026 ± 0.001 | 110 ± 11 | $0.23 \times 10^{-3}$ | 0.03 |
| 0 (C) | ND1 | dGTP | 0.10 ± 0.01 | 1.2 ± 0.2 | $85 \times 10^{-3}$ | 1 |
| 0 (C) | ICL4 | dGTP | 0.022 ± 0.001 | 1.8 ± 0.4 | $12 \times 10^{-3}$ | 0.14 |

Example 5

Cellular Responses to Mitomycin C Exposure in pol κ-Depleted Cells

Figures 3A, 3B, 3C:
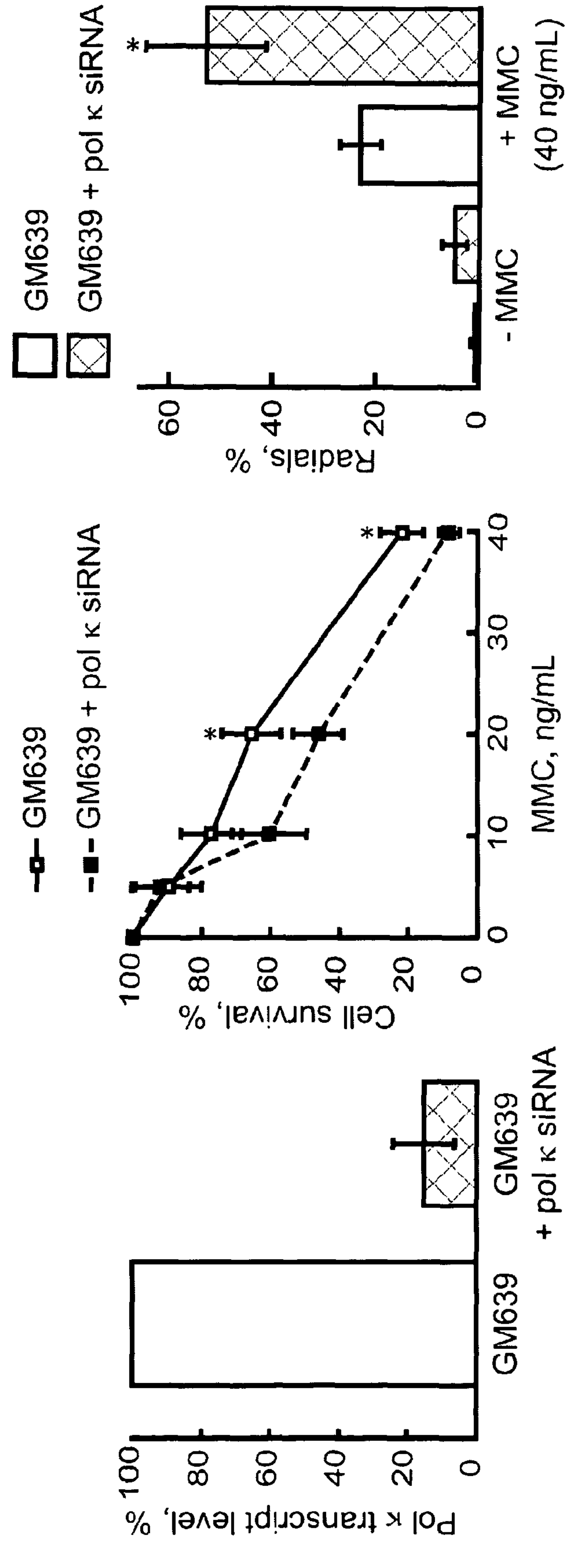
FIGS. 3A-3C are graphs showing cellular responses to mitomycin C (MMC) exposure in pol κ-depleted GM639 cells. Shown are pol κ transcript levels following treatment by a specific siRNA (A); relative colony-forming ability (B); and radial formation (C). Error bars represent standard errors for at least four independent experiments and data points marked with an asterisk indicate $P<0.05$ (relative to corresponding control).

In order to determine if pol κ functions intracellularly in the processing of $N^2$-$N^2$-guanine ICLs, the cytotoxicity of mitomycin C (MMC) in pol κ-depleted human cells was assessed. GM639 cells were treated with pol κ-specific siRNAs (SEQ ID NOs: 17-20) that were shown to reduce pol κ transcript level by approximately 85% (FIG. 3A). When subsequently challenged with MMC, the pol κ-depleted cells showed decreased survival versus mock-transfected cells (FIG. 3B). To seek additional biological evidence for a role for pol κ in the repair of these ICLs, mock-transfected and pol κ-depleted cells were examined for chromosomal damage in the form of radial formation. An increased frequency of radial formation is known to correspond with defective ICL repair in Fanconi anemia cells (Bruun et al., *DNA Repair* (Amst) 2:1007-1013, 2003; Sasaki, *Nature* 257:501-503, 1975). Following MMC treatment, the percent of cells containing radial structures was significantly increased in pol κ-depleted versus control cells (FIG. 3C). Combined, these data are strongly consistent with a biologically relevant role for pol κ in TLS-assisted repair of $N^2$-$N^2$-guanine ICLs in human cells.

Example 6

Figure 4:
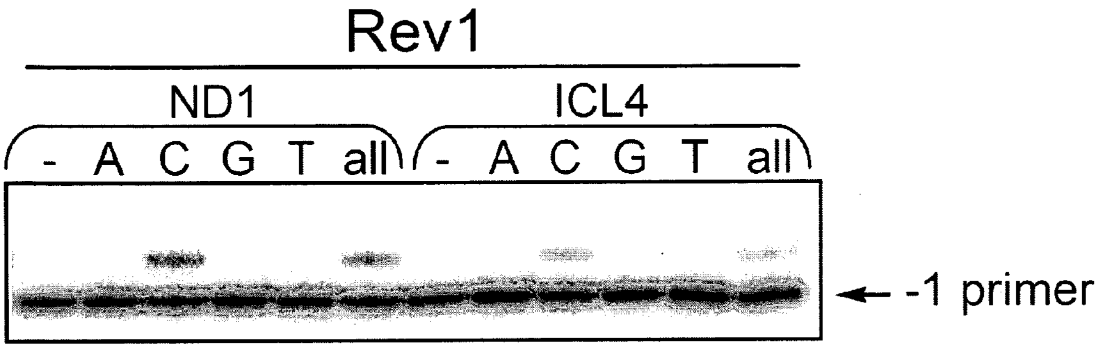
FIG. 4 shows replication bypass of ICLs by yeast Rev1. Primer extensions (marked 'all') and single nucleotide incorporations by Rev1 (10 nM) were carried out for 30 minutes.

Replication Bypass of Model Acrolein-Derived $N^2$-$N^2$-Guanine ICLs by Yeast Rev Previous studies have shown that recombination-independent repair of MMC-induced ICLs was less efficient in Rev1-deficient mutant cells relative to the wild type (Shen et al., *J. Biol. Chem.* 281:13869-13872, 2006), while in vitro, Rev1 strongly favored dCTP incorporation opposite $N^2$-adducted guanines (Washington et al., *Mol. Cell. Biol.* 24:6900-6906, 2004). Thus, the ability of Rev1 to insert nucleotides opposite the ICL4 was examined (FIG. 4). These data revealed that on both non-damaged (ND1) and ICL4 templates, Rev1 inserted a nucleotide opposite G, but could not extend the primer further. In reactions supplemented with individual dNTPs, insertion products were detected in the presence of dCTP exclusively (FIG. 4). As measured from three independent experiments, the rate of incorporation opposite the undamaged versus crosslinked G was $(1.84\pm0.31)\times10^{-3}$ $min^{-1}$ to $(0.70\pm0.03)\times10^{-3}$ $min^{-1}$. Thus, for an ICL containing a crosslinked G in a CpG local sequence context, Rev1 can accurately incorporate the first nucleotide.

Example 7

Figure 5A:
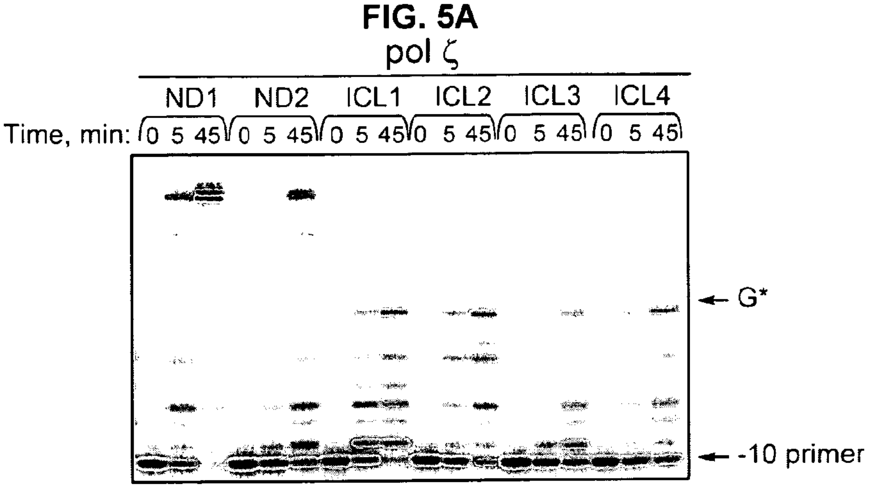
FIGS. 5A-5D show replication bypass of ICLs by yeast pol ζ. Primer extensions by pol ζ (5 nM) were conducted for a period of time as indicated (A). Single nucleotide incorporations by pol ζ (5 nM) were carried out for 30 minutes (B). Primer extension was carried out for 30 minutes at increasing concentrations of pol ζ (5, 10, or 20 nM) and Rev1 (5, 10, or 20 nM). Polymerases were present in reactions either individually or in combination (C). Primer extensions in the presence of pol ζ (10 nM) or a combination of pol ζ (10 nM) and Rev1 (10 nM) were carried out for 45 minutes (D).
Figure 5B:
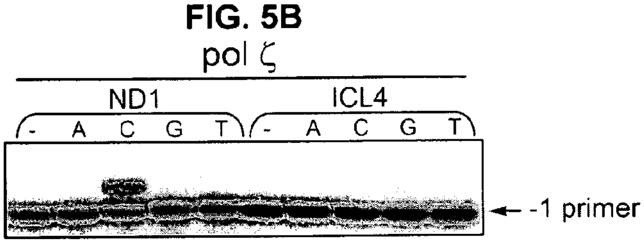
Figure 5C:
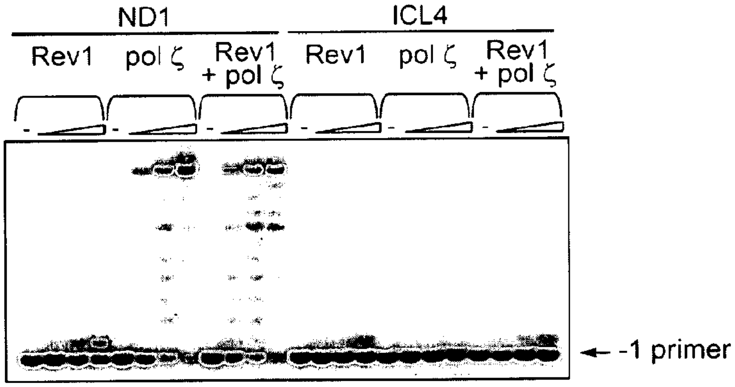

Inability of Yeast pol ζ to Catalyze Replication Bypass of Model Acrolein-Derived $N^2$-$N^2$-Guanine ICLs Cumulative genetic data support an involvement of pol ζ in the tolerance to MMC-induced damage and suggest a role for its contribution to MMC-associated mutagenesis (Shen et al., *J. Biol. Chem.* 281:13869-13872, 2006; Nojima, et al., *Cancer Res.* 65:11704-11711, 2005). However, a diploid yeast mutant that is deficient in rev3 does not show significantly elevated cytotoxic sensitivity following exposure to MMC (Wu et al., *Cancer Res.* 64:3940-3948, 2004). In addition, pol ζ has been proposed to play a role in TLS past $N^2$-guanine adducts by efficiently extending a C that had been inserted opposite the lesion by Rev1 (Washington et al., *Mol. Cell. Biol.* 24:6900-6906, 2004). Here, the ability of yeast pol ζ to bypass $N^2$-$N^2$-guanine ICLs was examined. As shown in FIG. 5A, using undamaged templates, pol ζ efficiently extended primers to yield products up to full-length DNA. In contrast, replication of all four ICL templates was completely blocked one nucleotide prior to the crosslinked guanine. In order to verify the inability of pol to catalyze nucleotide incorporation opposite the template ICL, a −1 primer was hybridized to the unadducted control template (ND1) and the ICL4, and reactions conducted in the presence of each individual dNTP. Error-free insertion of dCTP by pol ζ was observed using ND1 with approximately 25% of primers being extended; however, no incorporation of any dNTP could be detected using the ICL4 template (FIG. 5B). Next, the possibility that bypass of the crosslink could be accomplished by sequential action of Rev1 and pol ζ was evaluated. In this model, pol ζ would extend from a C that had been inserted opposite the crosslinked G by Rev1. Primer extension experiments were conducted in the presence of all four dNTPs and both Rev1 and pol ζ using a −1 primer that was annealed to either undamaged or ICL4 template. Under conditions when approximately 84% of primers were utilized in the presence of these proteins with undamaged template, no primer extension was observed beyond an ICL site (FIG. 5C).

Figure 5D:
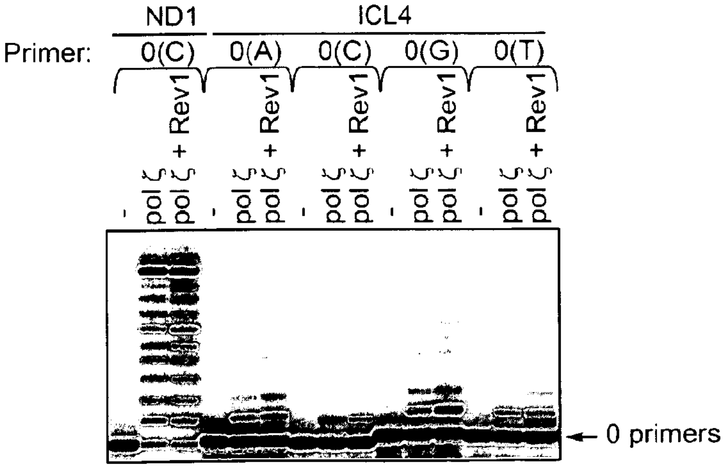

Additional reactions were carried out with pol ζ using a 0 primer that contains a C at its 3' end. Since Rev1 can stimulate the activity of pol ζ (Acharya et al., *Mol. Cell. Biol.* 26:9555-9563, 2006), primer extensions were also performed using a combination of these proteins. As shown in FIG. 5D, pol ζ alone efficiently extended primers annealed to undamaged template (about 89% of primer utilization) and showed similar efficiency in the presence of Rev1 (approximately 91% of primer utilization). In contrast, extension by pol ζ from a C opposite the crosslinked G (ICL4 template) appeared to be very inefficient with only about 7% of primers being extended, and little stimulation of polymerization by Rev1 was observed. In parallel reactions, a series of mismatched primers were tested. These primers were extended by pol ζ better than the correctly paired primer (about 19, 21, and 10% of primers were extended when A, G, and T were placed opposite the crosslinked guanine, respectively). This error-prone DNA synthesis was enhanced in the presence of Rev1 (FIG. 5D) with about 29, 33, and 16% of the corresponding primers being extended. Thus, replication bypass of $N^2$-$N^2$ guanine ICLs by pol ζ was highly inefficient and error-prone.

Example 8

Materials and Methods for Studies in *E. coli*

Modified oligodeoxynucleotides (FIG. 1C) (ICL1, ICL2, ICL3 and ICL4) containing various model acrolein-mediated $N^2$-$N^2$-guanine crosslinks (FIG. 1A) were synthesized and purified as described in Example 1. *E. coli* DNA pol II and pol IV were purified as previously described (Cai et al., *Methods Enzymol* 262, 13-21, 1995; Kobayashi et al., *J. Biol. Chem.* 277:34198-34207, 2002).

DNA Polymerase Bypass Assays

The primers (FIG. 1D) were $^{32}$P-end-labeled and annealed with the DNA templates as previously described (Minko et al., *J. Biol. Chem.* 278:784-790, 2003). The primer extension assays were conducted in a 10 μl reaction volume containing pol II or pol IV, 5 nM primer-template, 5 mM $MgCl_2$, 100 μM dNTPs, 25 mM Tris-HCl (pH 7.5), 25 mM DTT, 0.5 mg/ml BSA and 10% glycerol. Reactions were carried out at 37° C. for 30 minutes followed by termination of the reaction with a solution containing 95% formamide, 10 mM EDTA and 0.03% (w/v) xylene cyanol and 0.03% (w/v) bromophenol blue. DNA replication products were separated through a 15% denaturing polyacrylamide gel at 2000 V and later analyzed on a Phosphor Imager (GE Healthcare).

Steady-state kinetic assays were performed according to a standard procedure (Creighton et al., *Methods Enzymol.* 262: 232-256, 1995; Creighton and Goodman, *J. Biol. Chem.* 270, 4759-4774, 1995). Briefly, reactions were conducted at 22° C. in the same buffer as primer extension assays with the addition of NaC1 (50 mM). The concentration of the primer/template DNA substrates was 10 nM. Concentrations of pol IV and incubation times were adjusted for each particular primer-template combination such that the formation of the product would not exceed 25%. Nucleotide concentrations (dCTP and dGTP) varied. Quantitative analyses were performed using Image-Quant 5.2 software (Molecular Dynamics, Sunnyvale, CA). The rates of nucleotide incorporation were plotted as a function of nucleotide concentration, and the $k_{cat}$ and $K_m$ parameters were obtained from the best fit of the data to the Michaelis-Menten equation using KALEIDA-GRAPH™ 3.6 software (Synergy Software).

Bacterial Strains

The strains used in this study were derived from *E. coli* K12 strain W3110 and were isogenic except for deletion of either dinB or polB (Yeiser et al., *Proc. Natl. Acad. Sci. U.S.A.* 99:8737-8741, 2002; Zambrano et al., *Science* 259:1757-1760, 1993) (Table 4). All strains were cultured in Luria-Bertani broth (LB) containing appropriate antibiotics (100 μg/ml spectinomycin for pol II mutant, 50 μg/ml kanamycin for pol IV mutant).

TABLE 4

*E. coli* Strains

| Strain | Genotype | Relevant phenotype(s) |
|---|---|---|
| ZK126 | W3110 DlacU169 tna2 | Wild-type parental strain |
| SF2003 | ZK126 polB::Spc | Pol $II^-$ |
| SF2006 | ZK126 dinB::Kan | Pol $IV^-$ |

Generation of Vector Construct Carrying a Site-Specific $N^2$-$N^2$-Guanine Crosslink Characterization and preparation of a single-stranded pMS2 vector have been reported previously (Moriya et al., *Proc. Natl. Acad. Sci. U.S.A.* 85:1586-1589, 1988; Kanuri et al., *J. Biol. Chem.* 277:18257-18265, 2002). The single-stranded pMS2 DNA (15 pmoles), that carries an EcoRV site in its hairpin region, was linearized by digestion with EcoRV (100 units) for 3 hours at 37° C. and purified using Amicon 100K centrifugal filter devices according to manufacturer's protocol. A 36-mer oligodeoxynucleotide (CpG ICL; FIG. 1B) carrying a site-specific $N^2$-$N^2$-guanine ICL was designed in such a way that its single-stranded regions were complementary to the peripheral regions of the linearized pMS2 vector. The 36-mer oligodeoxynucleotide (15 pmoles) was phosphorylated using T4 polynucleotide kinase (50 units) for 1 hour at 37° C., added to linearized pMS2 vector, annealed, and extended using Klenow fragment of *E. coli* DNA pol I (25 units). A double-stranded linear product was gel-purified using Qiagen kit and ligated overnight at 12° C. with T4 DNA ligase (4,000 units). The ligated sample was designated as pMS2-ICL and further used for transforming *E. coli* cells.

Transformation of *E. coli* Strains with pMS2-ICL and pBR322 Plasmids

Initial experiments were conducted using wild-type *E. coli* cells to determine the amount of pMS2-ICL that in its transformation efficiency, would be comparable with 0.5 ng of the reference plasmid, pBR322. For both pMS2-ICL and pBR322, selection of successful transformants was done using resistance to ampicillin. Next, a mixture of plasmids containing pMS2-ICL and pBR322 was prepared at quantities that would provide approximately equal transformation efficiencies, and this mixture was utilized to transform individual *E. coli* strains. Transformations were done by electroporation as previously described (Kanuri et al., *J. Biol. Chem.* 277:18257-18265, 2002).

For further screening, the transformants were individually grown first in LB broth containing ampicillin (100 μg/ml) in 96-well plates at 37° C. for 4-6 hours. A 20 μl aliquot from each 96 well was transferred to another 96-well plate containing LB broth with tetracycline (12.5 μg/ml) and grown overnight at 37° C. Plasmids were isolated from tetracycline sensitive colonies, thus positive for carrying pMS2-ICL, and subjected to DNA sequencing using as a primer an 18-mer oligodeoxynucleotide (AGCAACCATAGTCCCGCC; SEQ ID NO: 14).

Example 9

In Vitro Replication Bypass of ICL-Containing DNA Substrates

Prior genetic evidence provides strong support for a role of *E. coli* DNA pol II in an HR-independent ICL repair pathway (Berardini et al., *Biochemistry* 36:3506-3513, 1997; Berardini et al., *J. Bacteriol.* 181:2878-2882, 1999). Based on these data and previous models, it was hypothesized that pol II could be responsible for the replication bypass of a 12-mer DNA strand that was still covalently attached to the template strand. This structure would be representative of the product of a dual incision by *E. coli* UvrABC around an ICL site. Experiments were designed to test the ability of *E. coli* pol II and IV to catalyze TLS on DNA substrates containing a site-specific ICL (FIG. 1C). Specifically, DNA strands in each of the four ICL substrates (ICL1, ICL2, ICL3, and ICL4) are joined via $N^2$-guanines in a CpG sequence context using a carbon bridge that models an acrolein-derived ICL (FIG. 1A). ICL1 models the result of incision by the UvrABC complex, while ICL2 and ICL3 represent intermediates in which nucleotides 5' and 3' to the ICL respectively, have been removed. ICL4 contains a residual ICL in which nucleotides both 5' and 3' have been removed. The 3' ends of ICL1 and ICL2 are terminated with a dideoxynucleotide ((dd)-3') to prevent any synthesis from the crosslinked strand. Similarly, ICLs 3 and 4 are 3' capped with a glycerol (gl-3') to prevent replication from that site. $^{32}$P-labelled primers were designed to initiate synthesis 1 or 10 nucleotides 5' to the crosslinked site in the template strand. A 0 primer was used to initiate the replication from C opposite to the crosslinked G.

Figure 7A:
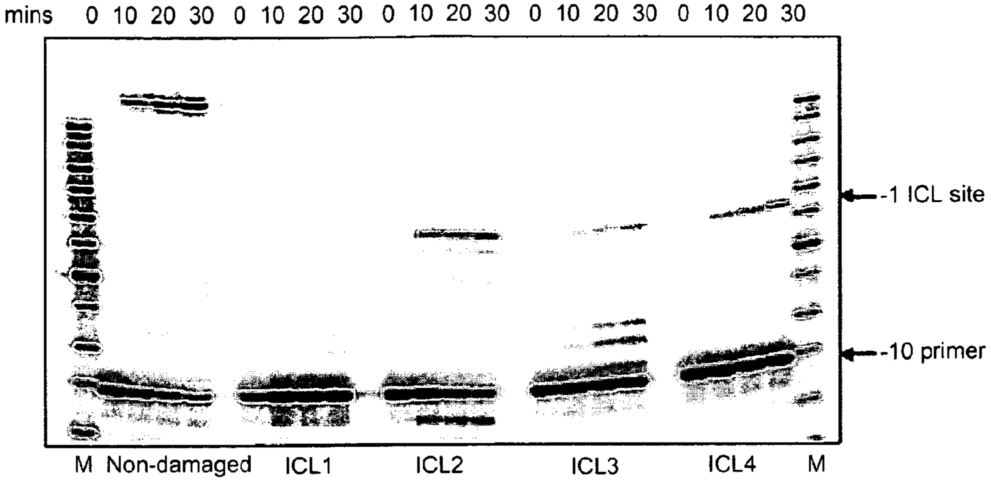
FIGS. 7A-7C show primer extension by pol II (A) and pol IV (B). A time-course primer-extension experiment was conducted on ICL DNA substrates 1-4 and non-damaged template (ND1). A −10 primer (10 bases upstream of the adduct site) was annealed to the DNA template and incubated with pol II or pol IV (0.3 nM) for the indicated times. Primer extension activity by DNA pol IV is dose-dependent (C). This experiment was conducted on ICLs 1-4 primed with −10 primer with increasing concentrations of pol IV at 37° C. for 30 minutes.
Figure 7B:
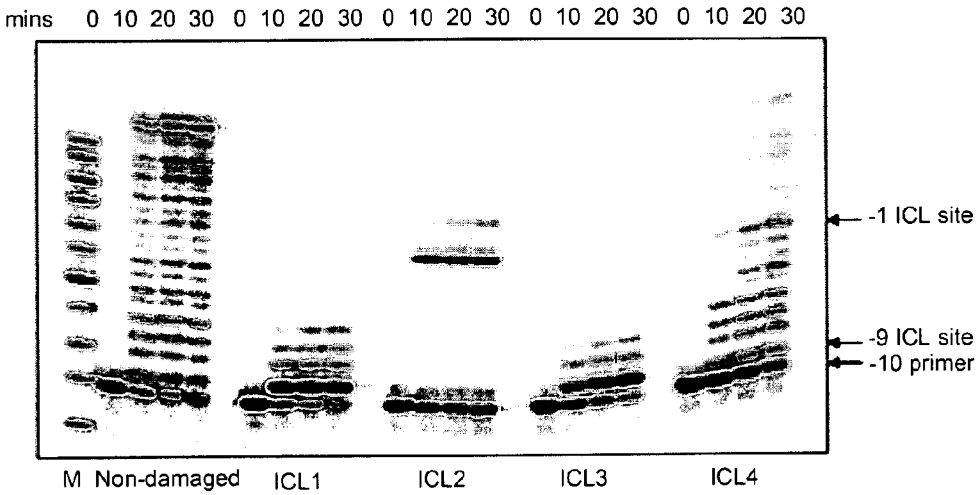
Figure 7C:
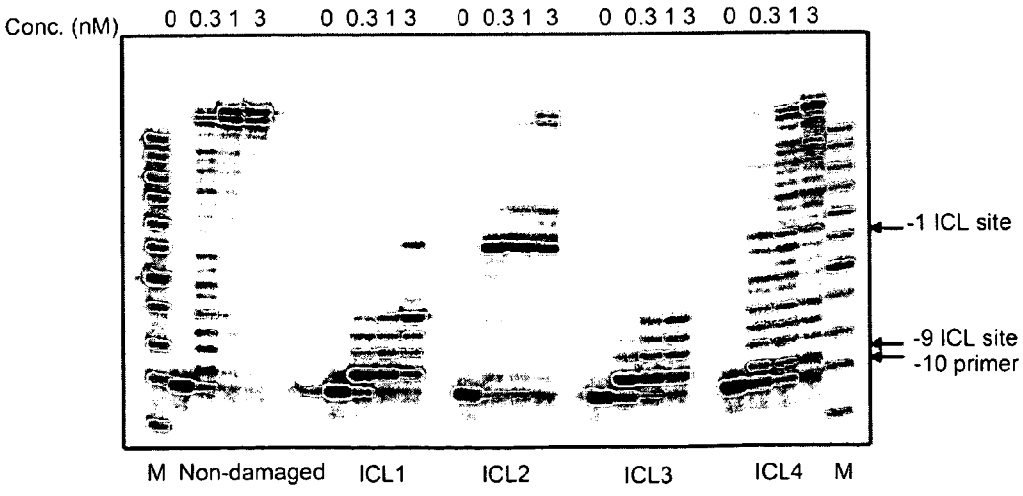

Control, non-damaged and ICL-containing DNA substrates were used to analyze replication from a −10 primer by pol II (FIG. 7A) and pol IV (FIGS. 7B and 7C). Using the non-damaged primer-template substrates pol II catalyzed a highly processive polymerization to yield full-length primer extension products. However, under identical conditions, pol II was unable to carry out effective strand-displacement synthesis on ICL1 and ICL3, while on ICL2 and ICL4, it could replicate up to one nucleotide prior to the crosslinked guanine, but no TLS past the lesion was observed (FIG. 7A). ICL bypass by pol II was not observed even when reactions were conducted with increased enzyme concentrations (up to a 1000-fold excess relative to DNA substrate).

Examination of the activities of pol IV on the same substrates revealed a less processive synthesis on the non-damaged DNA template and a very poor ability to catalyze strand displacement synthesis on ICLs 1 and 3, following the incorporation of the first nucleotide (FIG. 7B). Using the ICL2 primer-template in which no strand displacement synthesis is necessary, pol IV was able to synthesize up to one nucleotide prior to the ICL, but was only able to catalyze minimal incorporation opposite the lesion; further synthesis was blocked two nucleotides beyond the crosslinked site. In contrast, pol IV synthesis on the ICL4 primer-template revealed that although multiple pause sites occurred prior to reaching the ICL, there was only modest blockage at the lesion (FIG. 7B). Following incorporation opposite the crosslinked nucleotide, synthesis continued with reduced processivity with full-length DNA products accumulating over time.

Given these data, 30-minute reactions were conducted using increasing concentrations of pol IV (FIG. 7C). Again, very poor strand displacement synthesis was observed on ICL1 and ICL3, while replication bypass was readily measured on ICL4 and to a lesser extent on ICL2. These data suggest that pol IV can catalyze TLS past $N^2$-guanine ICLs; however, 5' resection leading up to the lesion and 3' exonucleolytic processing increase the TLS efficiency.

Figure 8:
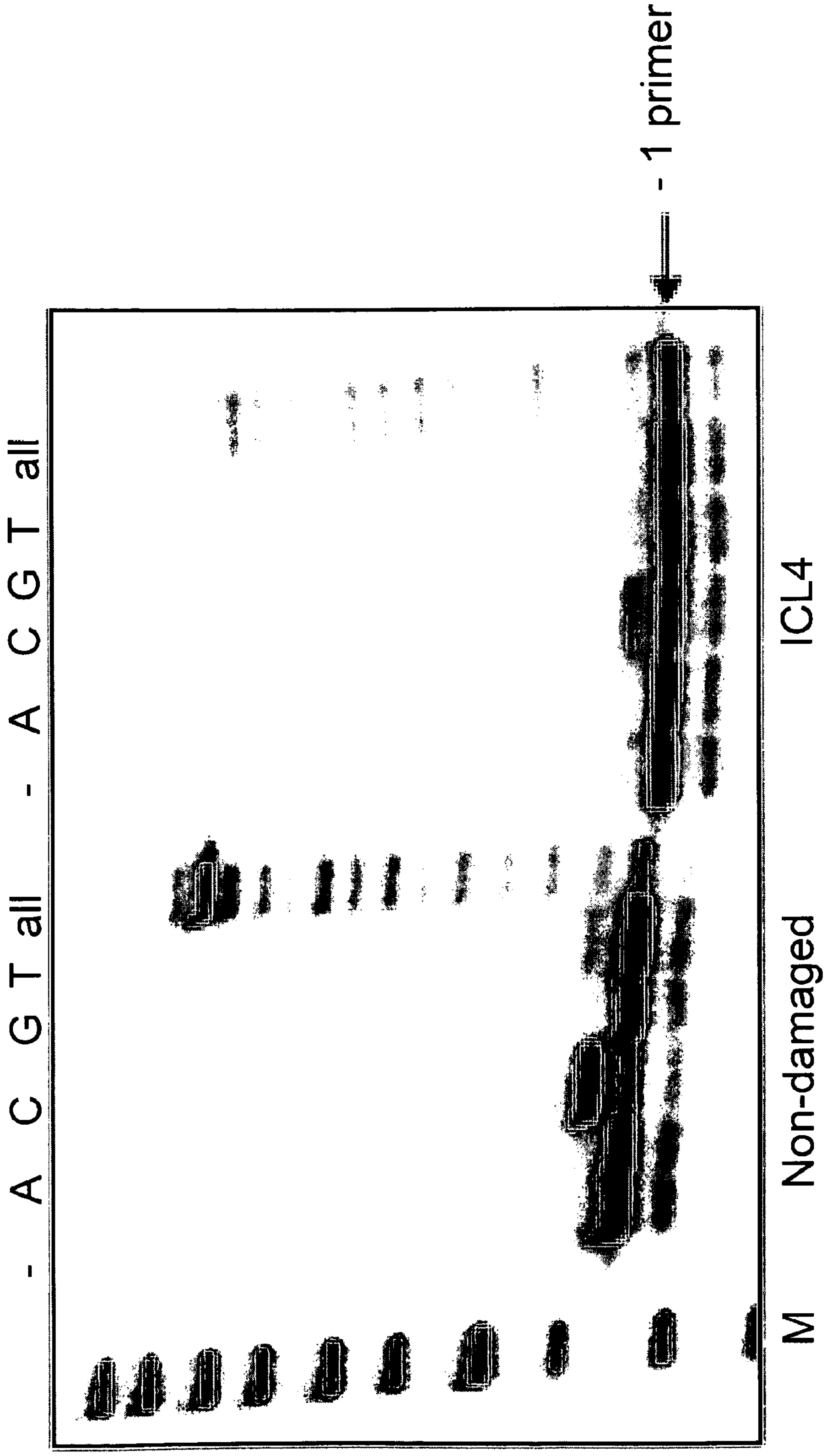
FIG. 8 shows the results of a single nucleotide incorporation assay. Fidelity of pol IV (0.3 nM) to incorporate nucleotides opposite the $N^2$-$N^2$-guanine adduct was assessed using the −1 primer annealed to ICL4 or non-damaged template (5 nM) in the presence of individual nucleotides (25 μM). These experiments were carried out for 30 minutes at 37° C.

In order to determine the identity of nucleotide(s) inserted by pol IV opposite the crosslinked guanine, qualitative single nucleotide incorporation assays were conducted using a −1 primer annealed to ICL4. These data revealed that pol IV faithfully incorporated a dCTP opposite the lesion site (FIG. 8). Steady-state kinetic analyses showed that the catalytic efficiency ($k_{cat}/K_m$) of dCTP incorporation opposite the crosslinked G relative to the control G was reduced approximately 50-fold, while efficiency of extension from a C opposite the crosslinked G was reduced approximately 2-fold (Table 5).

TABLE 5

Steady-state kinetic parameters for ICL bypass by *E. coli* DNA pol IV

| DNA substrate | Primer | dNTP | $k_{cat}$ ($min^{-1}$) | $K_m$ (mM) | $k_{cat}/K_m$ ($\mu M^{-1}min^{-1}$) | Relative efficiency |
|---|---|---|---|---|---|---|
| ND1 | −1 | dCTP | 0.90 ± 0.08 | 168 ± 30 | $5.4 \times 10^{-3}$ | 1 |
| ICL4 | −1 | dCTP | 0.020 ± 0.001 | 183 ± 18 | $0.11 \times 10^{-3}$ | 0.02 |
| ND1 | 0 | dGTP | 3.9 ± 0.2 | 85 ± 8 | $46 \times 10^{-3}$ | 1 |
| ICL4 | 0 | dGTP | 0.75 ± 0.02 | 36 ± 3 | $21 \times 10^{-3}$ | 0.46 |

Example 10

Replication of ICL-Containing Plasmid DNAs in *E. coli*

To explore cellular role for *E. coli* polymerases in processing of $N^2$-$N^2$-guanine ICLs, a double-stranded plasmid vector carrying a site-specific $N^2$-$N^2$-guanine crosslink was generated (CpG ICL, FIG. 1B) and this modified DNA was utilized to transform wild-type, pol II and pol IV mutant *E. coli* strains. The efficiency of transformation was evaluated relative to a reference plasmid, unmodified pBR322. The pBR322 plasmid encodes resistance to both ampicillin and tetracycline, whereas pMS2-ICL can be only selected when cells are challenged with ampicillin. This feature allowed for a distinction between the cells transformed with pBR322 versus the ones transformed with pMS2-ICL. The bacterial cells were electroporated with a cocktail of pBR322 and pMS2-ICL and were grown on LB agar plates containing ampicillin. For further screening, 192 transformed colonies were selected per strain, and a ratio of transformants carrying pBR322 versus those transformed with pMS2-ICL was determined by growing them first in LB broth with ampicillin followed by transferring an aliquot of culture to LB broth containing tetracycline.

Figure 9:
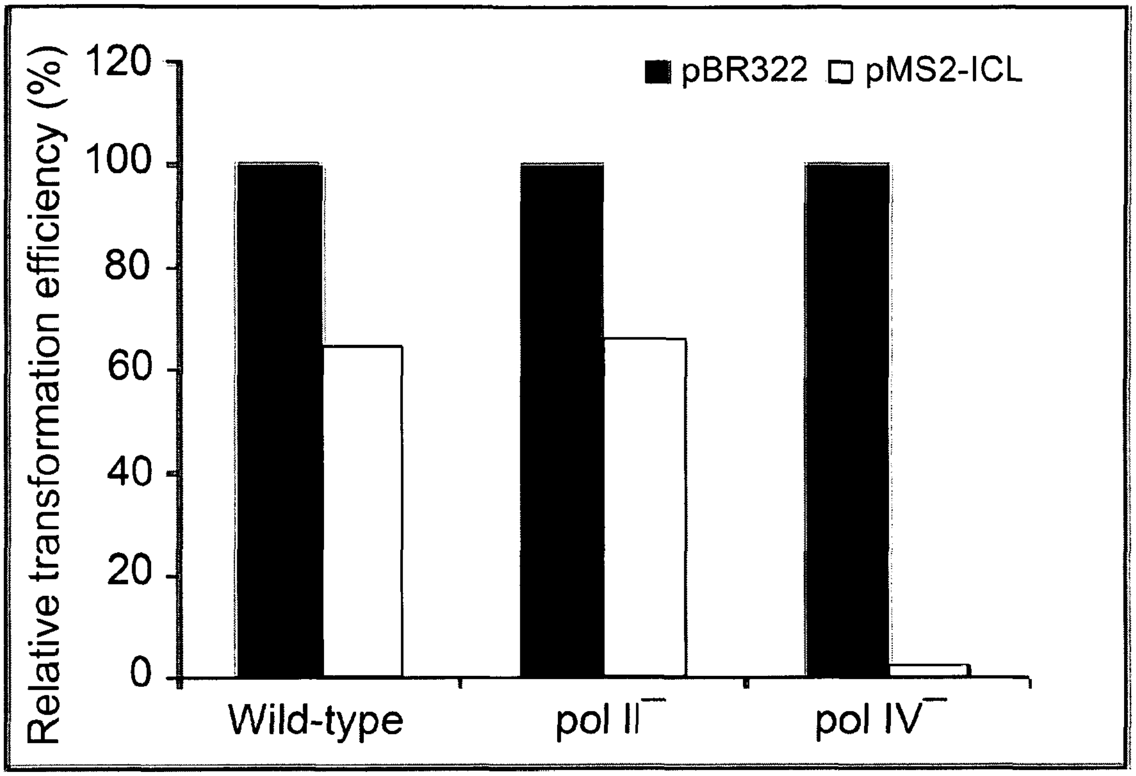
FIG. 9 is a graph showing relative colony forming ability of *E. coli* strains following transformation with an ICL containing plasmid. For each strain, the percentage of pMS2-ICL transformants was calculated relative to pBR322 transformants. The apparent transformation efficiency with the reference plasmid (pBR322) was comparable for all the strains tested.

For wild-type cells and pol II mutant, out of 192 transformants tested, 76 and 75 transformants respectively, were found to be tetracycline negative and thus positive for carrying plasmids that originated from pMS2-ICL (FIG. 9). Plasmids were isolated from a subset of pMS2-ICL transformants (10 for pol II mutants and 52 for wild-type), and the region of modification was analyzed by DNA sequencing. In all these plasmids, the insert sequences were present and no mutations were detected. Therefore, in the absence of pol II no effect was observed on intracellular replication of $N^2$-$N^2$-guanine ICL-containing DNA.

Using the pol IV deletion mutant, the relative efficiency of transformation with pMS2-ICL was in contrast, extremely low; out of 192 transformants only 5 were tetracycline negative. When plasmids isolated from these transformants were subjected to DNA sequencing, 3 out of 5 contained the insert sequences with no alterations, while 2 others were homologous to re-ligated pMS2 vectors without inserts. Thus, relative to wild type, the efficiency of transformation with plasmids containing $N^2$-$N^2$-guanine ICL was reduced by approximately 40-fold in pol IV-deficient strain. These data indicate that pol IV is essential for cellular processing of $N^2$-$N^2$-guanine ICLs. The yield of non-adducted pBR322 transformed progenies remained almost comparable for the wild-type, and pol II and pol IV mutants.

For all the strains, sequence analysis of the screened progenies originating from pMS2-ICL, did not reveal any deletions or point mutations at the adducted site or the neighboring bases. Thus, recombination-independent repair of $N^2$-$N^2$-guanine ICLs in *E. coli* is essentially non-mutagenic. Given an accurate bypass of these ICLs by pol IV in vitro and based the results from plasmid-based assays, it is likely that pol IV is primarily responsible for the non-mutagenic processing of $N^2$-$N^2$-guanine crosslinks in vivo.

Example 11

Identification of Small Molecule Inhibitors of pol κ

This example describes a method for identification of small molecule inhibitors of DNA polymerases, such as DNA pol κ, using a high throughput, automated screen. The screening assay is based on the inhibition of incorporation of fluorescently labeled nucleotides into duplex DNA as catalyzed by DNA polymerases. A basic assay for the screening of any DNA polymerase inhibitor is performed according to the method described below and shown in FIG. 10.

The template oligodeoxynucleotide used in this assay is 40 nucleotides in length and has the following features in the 5' to 3' direction: (i) 5'-OH (which can be phosphorylated as needed); (ii) a 12 nucleotide poly dT or poly dA track that serves as the template strand for the incorporation of fluorescently-labeled nucleotides (or other spectroscopically detectable nucleotides); (iii) five nucleotides that can be composed of any combination of the three nucleotides that are not found in either the poly dA or poly dT tract at the 5' most end of the oligodeoxynucleotide (for example, if a poly dT is at the 5' end, any combination of A, G, and C can be used in this five-nucleotide segment); (iv) an 18-nucleotide primer binding sequence CGCAAGGTAGCACTCAGG (SEQ ID NO: 15); (v) a linker sequence of five nucleotides (or a peptide linker) that serves as a flexible linkage between the primer-template junction and the site of attachment to the solid matrix support; and (vi) a biotin-conjugated nucleotide at the 3' terminus. The biotin conjugate is used to attach the template strand to a solid matrix coated with avidin. Functionally analogous two-component binding systems can be substituted for the biotin-avidin linkage.

The primer oligodeoxynucleotide (CCTGAGTGCTACCTTGCG; SEQ ID NO: 16) used in this assay is complementary to the 18-nucleotide primer binding sequence. Equal molar concentrations of the primer and template oligodeoxynucleotide are mixed in a solution that is buffered to a physiologically relevant pH (approximately pH 7.4) using a common buffer solution (for example, 25 mM Tris HCl, Na/K phosphate, or HEPES) and 10 mM $MgCl_2$. The solution is warmed to approximately 70° C. (about 12° C. above the melting temperature of the primer/template), and slow cooled to about 22° C.

The primer/template is aliquotted into 96 or higher number well plates that have been coated with avidin, such as by automated fluid handling robotics. The specific DNA polymerase is added to each well, except for pre-selected polymerase-negative wells. The molarity of the polymerase added will be predetermined in small-scale assays. The candidate inhibitor compounds are added to individual wells, such as by automated fluid handling robotics. As controls, each plate includes a series of wells containing known DNA replication inhibitors (such as 20 mM EDTA).

The polymerase reactions are initiated by the addition of the dNTPs at 10 μM (dGTP, dCTP, dATP if the polynucleotide run in the template stand is a poly dA, or dGTP, dCTP, dTTP if the polynucleotide run in the template strand is a poly dT) and either 1.0 to 10 μM of a fluorescently labeled dTTP or dATP, as appropriate. The temperature of the reaction is raised to 37° C. and proceeds for 30 minutes.

Each well is washed three times with a buffer that contains a divalent metal chelation compound in order to terminate polymerization and remove any unincorporated fluorescently-labeled dNTP. Buffer is added that is compatible with automated fluorescence detection systems and the plates scanned for the level of fluorescence that has been incorporated opposite the poly dA or poly dT track. If a candidate small molecule inhibitor compound is successful in preventing polymerization, this will be manifested by a lack of (or reduced) incorporation of the fluorescent dNTP, and thus little or no signal detected.

Example 12

Use of a pol κ Inhibitor as an Adjunctive Therapy for Treatment of Head and Neck Cancer This example describes a treatment regimen for a subject diagnosed with head and neck squamous cell carcinoma that includes use of a pol κ inhibitor. A subject diagnosed with head and neck cancer undergoes surgical resection of the tumor, followed by concurrent radiation and chemotherapy according to methods known in the art (see, for example Cooper et al., *N. Engl. J. Med.* 350(19):1937-1944, 2004). The subject receives radiation therapy including 60-66 Gy in 30-33 fractions over a period of approximately 6 weeks. On days 1, 22 and 43, the subject is administered cisplatin intravenously at a dose of 100 $mg/m^2$ of body surface area. The subject is further administered a small molecule inhibitor of pol κ on days 1, 22 and 43.

Example 13

Use of a pol κ Inhibitor for the Treatment of Autoimmune Disease

This example describes a treatment regimen for a subject diagnosed with rheumatoid arthritis. A subject with active, refractory rheumatoid arthritis is administered cyclophosphamide intravenously at a dose of 50 mg/kg/day for four consecutive days according to methods known in the art (see, for example, Verburg et al., *Arthritis Rheum.* 52(2):421-424, 2005). The subject is concurrently administered a small molecule inhibitor of pol κ. The subject is evaluated for clinical signs of disease. Additional doses of cyclophosphamide in combination with the pol κ inhibitor are administered as needed.

Example 14

Topical Treatment with a pol κ Inhibitor and Mitomycin C

This example describes the use of a pol κ inhibitor in combination with mitomycin C during trabeculectomy for the treatment of glaucoma. A subject diagnosed with glaucoma with uveitis is identified as a candidate for trabeculectomy. After anesthetic administration, a superior limbal peritomy is performed and hemostasis of the scleral bed is achieved using bipolar cautery. A sponge soaked in a pharmaceutical composition comprising approximately 0.2 mg/mL mitomycin C and a small molecule inhibitor of pol κ is placed under the conjunctiva for approximately 30 to 180 seconds. After removal of the sponge, the area is copiously irrigated with a balanced salt solution. The trabeculectomy procedure is carried out according to methods well known in the art (see, for example, Nobel et al., *Can. J. Ophthalmol.* 42:89-94, 2007).

This disclosure provides a method of enhancing the efficacy of an ICL-inducing agent. The disclosure further provides a method of identifying pol κ inhibitors. It will be apparent that the precise details of the methods described may be varied or modified without departing from the spirit of the described disclosure. We claim all such modifications and variations that fall within the scope and spirit of the claims below.

The invention claimed is:

1. A method of identifying an agent that inhibits the activity of a DNA polymerase, comprising:

(i) mixing a template oligodeoxynucleotide, a primer oligodeoxynucleotide and the DNA polymerase, wherein the template oligodeoxynucleotide comprises in the 5' to 3' direction:

(a) a 5'-OH, wherein the 5'-OH is phosphorylated or non-phosphorylated;

(b) a poly dT or a poly dA track of about 8 to about 16 nucleotides;

(c) a short segment of nucleotides about 3 to about 7 nucleotides in length, wherein the nucleotides include A, C and G when (b) is a poly dT track, or the nucleotides include T, C and G when (b) is a poly dA track;

(d) a primer binding sequence that is complementary to the nucleotide sequence of the primer oligodeoxynucleotide, wherein the primer binding sequence comprises the nucleotide sequence of SEQ ID NO: 15;

(e) a linker sequence;

(f) a biotin-conjugated nucleotide; and (g) 1 to 3 nucleotides at the 3' terminus;

(ii) adding unlabeled dNTPs and a fluorescently-labeled dTTP or dATP;

(iii) adding a candidate agent; and (iv) incubating the template oligodeoxynucleotide, the primer oligodeoxynucleotide, the DNA polymerase, the unlabeled dNTPs, the fluorescently-labeled dTTP or dATP, and the candidate agent for a sufficient period of time to allow DNA polymerization, wherein a reduction in incorporation of the fluorescently labeled dTTP or dATP in the presence of candidate agent, relative to incorporation of the fluorescently labeled dTTP or dATP in the absence of the candidate agent, indicates the candidate agent is an agent the inhibits the activity of a DNA polymerase.

2. The method of claim 1, wherein the poly dT or poly dA track is about 12 nucleotides in length.

3. The method of claim 1, wherein the short segment of nucleotides is about 5 nucleotides in length.

4. The method of claim 1, wherein the short segment of nucleotides comprises an interstrand crosslink (ICL).

5. The method of claim 1, wherein the primer binding sequence is 18 to about 24 nucleotides in length.

6. The method of claim 1, wherein the linker sequence is a nucleotide sequence.

7. The method of claim 1, wherein the template oligodeoxynucleotide is about 30 to about 50 nucleotides in length.

8. The method of claim 1, wherein the candidate agent is a small molecule.

9. The method of claim 1, wherein the 5'-OH is phosphorylated.

10. The method of claim 1, wherein the 5'-OH is non-phosphorylated.

11. The method of claim 1, wherein the template oligodeoxynucleotide comprises a poly dT track and the short segment of nucleotides of (iii) include A, C and G.

12. The method of claim 1, wherein the template oligodeoxynucleotide comprises a poly dA track and the short segment of nucleotides of (iii) include T, C and G.

13. The method of claim 1, wherein the primer binding sequence is 18 nucleotides in length.

14. The method of claim 6, wherein the linker sequence is about 3 to about 10 nucleotides in length.

15. The method of claim 1, wherein the linker sequence is an amino acid sequence.

16. The method of claim 7, wherein the template oligodeoxynucleotide is about 40 nucleotides in length.

17. The method of claim 1, wherein the primer oligodeoxynucleotide is 100% complementary to the primer binding sequence.

18. The method of claim 1, wherein step (ii) comprises adding fluorescently labeled dATP and unlabeled dTTP, dCTP and dGTP.

19. The method of claim 1, wherein step (ii) comprises adding fluorescently labeled dTTP and unlabeled dATP, dCTP and dGTP.

* * * * *

SEQUENCE LISTING

```
<160> NUMBER OF SEQ ID NOS: 20

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 1

gctagcgagt cc                                                         12


<210> SEQ ID NO 2
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 2

cctgcaagcg atggactcgc tagcatcgct ggtacc                               36


<210> SEQ ID NO 3
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 3

gctgagcgat cc                                                         12
```

<210> SEQ ID NO 4
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 4
cctgcaagcg atggatcgct cagcatcgct ggtacc 36

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t

<400> SEQUENCE: 5
gatgctancy tgtc 14

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 6
agcgatagac acyatagcat cgctggtacc gactcg 36

<210> SEQ ID NO 7
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 7
gatgctatcg tgag 14

<210> SEQ ID NO 8
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 8
cgagtcggta ccag 14

<210> SEQ ID NO 9
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 9
ggtaccagcg atgctat 17

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
ggtaccagcg atgctatc 18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
ggtaccagcg atgctata 18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
ggtaccagcg atgctatg 18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
ggtaccagcg atgctatt 18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
agcaaccata gtcccgcc 18

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
cgcaaggtag cactcagg 18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 16
cctgagtgct accttgcg 18

-continued

```
<210> SEQ ID NO 17
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 17

guacagaacu uuaccaacau u                                              21


<210> SEQ ID NO 18
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 18

gaugaagccu acuugaauau u                                              21


<210> SEQ ID NO 19
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 19

ggaugggacu uaaugauaau u                                              21


<210> SEQ ID NO 20
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 20

guagaacugu uaccauuaau u                                              21
```